United States Patent
Wooley et al.

(10) Patent No.: US 9,422,433 B2
(45) Date of Patent: Aug. 23, 2016

(54) TERNARY ANTIFOULING COMPOSITIONS AND METHODS

(71) Applicant: The Texas A&M University System, College Station, TX (US)

(72) Inventors: Karen L. Wooley, College Station, TX (US); Jeffery E. Raymond, College Station, TX (US); Kevin A. Pollack, Dallas, TX (US); Philip M. Imbesi, Gilbertsville, PA (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 14/575,625

(22) Filed: Dec. 18, 2014

(65) Prior Publication Data
US 2015/0307720 A1 Oct. 29, 2015

Related U.S. Application Data

(63) Continuation of application No. PCT/US2013/047070, filed on Jun. 21, 2013.

(60) Provisional application No. 61/663,165, filed on Jun. 22, 2012.

(51) Int. Cl.
*A01N 55/00* (2006.01)
*A01N 37/44* (2006.01)
*C08G 81/02* (2006.01)
*C08G 77/442* (2006.01)
*C08G 77/46* (2006.01)
*C09D 5/16* (2006.01)

(52) U.S. Cl.
CPC .............. *C09D 5/1637* (2013.01); *A01N 37/44* (2013.01); *A01N 55/00* (2013.01); *C08G 77/442* (2013.01); *C08G 77/46* (2013.01); *C08G 81/025* (2013.01); *C09D 5/1675* (2013.01); *C09D 5/1681* (2013.01)

(58) Field of Classification Search
CPC .. C09D 5/1637; C09D 5/1675; C09D 5/1681; C08G 81/025; C08G 77/442; C08G 77/46; A01N 37/44; A01N 55/00
See application file for complete search history.

(56) References Cited

U.S. PATENT DOCUMENTS

2011/0065882 A1 3/2011 Dai et al. .................... 528/26
2011/0281340 A1* 11/2011 Turner .................. C12M 21/02
435/257.1

FOREIGN PATENT DOCUMENTS

WO 2010/096024 8/2010 .............. C08F 2/38
WO 2011/069111 A1 6/2011 .............. C08L 27/12

OTHER PUBLICATIONS

Pollack et al. (ACS Applied Materials & Interfaces 2014, 6, 19265-19274).*
Bartles et al., "Hyperbranched Fluoropolymers and their Hybridization into Complex Amphiphilic Crosslinked Copolymer Networks", Macromol. Chem. Phys., vol. 208, Issue 15, pp. 1676-1687, Aug. 3, 2007.

(Continued)

*Primary Examiner* — Aradhana Sasan
(74) *Attorney, Agent, or Firm* — Baker Botts L.L.P.

(57) ABSTRACT

Compounds for mitigation of biofouling, and methods of making compounds for biofouling. Terpolymers comprising hyperbranched fluoropolymers possessing unique topology mitigate fouling on susceptible surfaces. In some embodiments, the terpolymers comprise PEG and PDMS.

49 Claims, 26 Drawing Sheets

(56) References Cited

OTHER PUBLICATIONS

International Search Report and Written Opinion; PCT/US2013/047070; 11 pages, Sep. 24, 2013.

Powell et al., "Complex Amphiphilic Hyperbranched Fluoropolymers by Atom Transfer Radical Self-Condensing Vinyl (Co)Polymerization", Macromolecules, vol. 40, No. 13, pp. 4509-4515, 2007.

Imbesi et al., "Noradrenaline-Functionalized Hyperbranched Fluoropolymer-Poly(ethylene glycol) Cross-Linked Networks as Dual-Mode, Anti-Biofouling Coatings", ACS Nano, vol. 6, No. 2, pp. 1503-1512, Jan. 2012.

Gudipati et al., "The Antifouling and Fouling-Release Performance of Hyperbranched Fluoropolymer (HBFP)-Poly(ethylene glycol) (PEG) Composite Coatings Evaluated by Adsorption of Biomacromolecules and the Green Fouling Alga *Ulva*", Centre for Materials Innovation and Department of Chemistry, vol. 21, No. 7, pp. 3044-3053, 2005.

European Extended Search Report, Patent Application No. 13807698.9, 8 pages, Nov. 20, 2015.

K. Pollack et al.; "Hyperbranched Fluoropolymer-Polydimethylsiloxane-Poly (ethylene glycol) Cross-Linked Terpolymer Networks Designed for Marine and Biomedical Applications: Heterogeneous Nontoxic Antibiofouling Surfaces", ACS Applied Materials and Interfaces, vol. 6, No. 21, pp. 19265-19274, Nov. 12, 2014.

H.S. Sundaram et al.: "Fluorine-Free Mixed Amphiphilic Polymers Based on PDMS and PEG Side Chains for Fouling Release Applications", Biofouling, vol. 27, No. 6, pp. 589-602, Jun. 22, 2011.

The First Office Action (PCT application in Chinese National Phase), Patent Application No. 201380044497.0, 13 pages, Nov. 17, 2015.

Shi Hang et al.; "Incorporation of NaB and PD MS Antifouling Coatings", New Chemical Materials, vo. 37, No. 9, pp. 44-45, 82, Sep. 30, 2009.

Singapore Written Opinion, Patent Application No. 11201408581S, 6 pages, Oct. 19, 2015.

\* cited by examiner

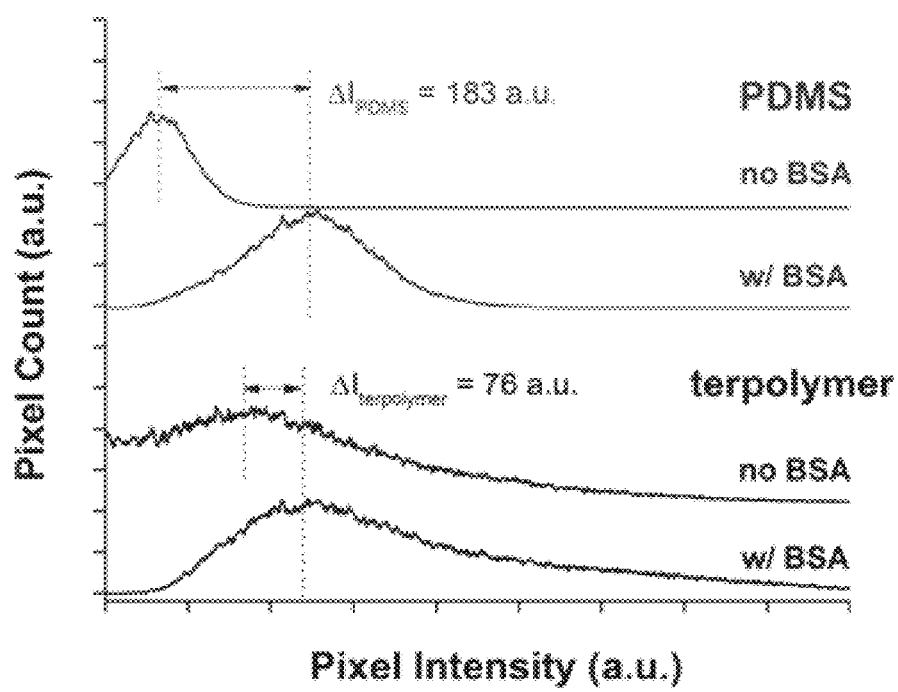
*FIG. 13A*
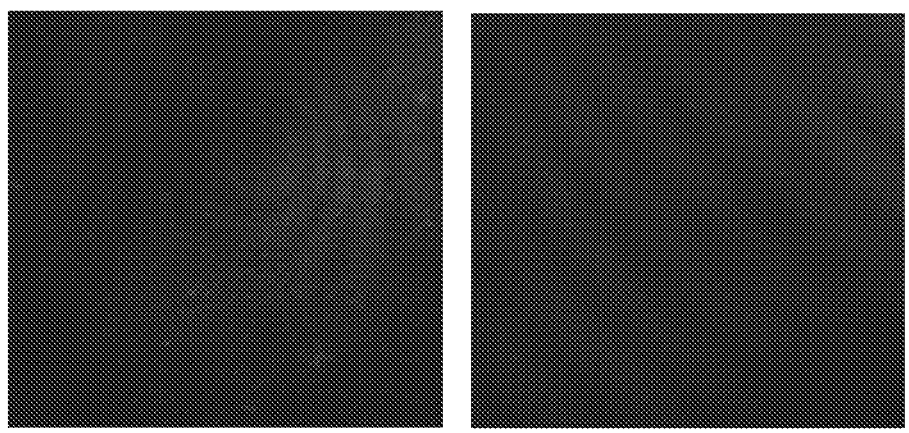
*FIG. 13B*  *FIG. 13C*

TERNARY ANTIFOULING COMPOSITIONS AND METHODS

STATEMENT OF GOVERNMENT INTEREST

This invention was made with government support under Grant No. N0014-10-1-0527 awarded by the U.S. Office of Naval Research. The government has certain rights in the invention.

BACKGROUND

Biofouling plagues a wide spectrum of applications, from medical devices to maritime vessels. For the latter, biofouling increases the fuel consumption of the vessel, in turn leading to increased operational and maintenance costs. Conventionally, the method of prevention has been through the use of anti-biofouling paints and coatings which release biocides, such as cuprous oxide and tributyltin; however, due to the negative effects these chemicals have on the environment, the use of these systems is in decline.

Fluoropolymers, siloxanes and poly(ethylene glycol) (PEG) have been researched extensively as anti-biofoulers due to their unique chemical compositions. Fluoropolymers are of particular interest due to a low surface energy, low wettability and chemical stability. Siloxanes, specifically poly(dimethylsiloxane) (PDMS), have shown anti-biofouling attributes due to their inertness, stability, and pliability. Commercially, PDMS coatings are marketed as non-toxic marine coatings due to the release and rejection of fouling agents under suitable hydrodynamic conditions. Poly(ethylene glycol) (PEG), or poly(ethylene oxide) (PEO), has been used extensively in the field of marine applications, as well as in the medical field due to its ability to generate surfaces that resist non-specific protein adsorption.

Biofouling can result from a number of mechanisms but generally involves protein adhesion and deposition by microorganisms or organisms to surfaces exposed to, and typically in fluid communication with, an environment which harbors the microorganisms or organisms. In maritime applications alone, the costs associated with maintenance, increased vessel drag, and other consequences of biofouling are billions of dollars per year.

There is a need to reduce biofouling of susceptible surfaces. Fluoropolymers, siloxanes and poly(ethylene glycol) (PEG) have been researched as anti-biofoulers due to their unique chemical compositions. Fluoropolymers are of particular interest due to a low surface energy, low wettability and chemical stability. Siloxanes, specifically poly(dimethylsiloxane) (PDMS), have shown anti-biofouling attributes due to their inertness, stability, and pliability. Commercially, PDMS coatings are marketed as non-toxic marine coatings due to the release and rejection of fouling agents under suitable hydrodynamic conditions. Poly(ethylene glycol) (PEG), has been used extensively in the field of marine applications, as well as in the medical field due to its ability to generate surfaces that resist non-specific protein adsorption. Previously, linear PDMS has been modified to include hydrophilic and fluorinated moieties. However, the chemistries involved incorporation of linear PDMS backbones with chemical variation achieved via side group modification. This approach is limited, as it does not address the topological influences of surfaces in preventing biofouling. Topological heterogeneity in conjunction with chemical heterogeneity can further improve anti-biofouling performance through the inhibition of adhesive proteins that settle on the surface. Therefore, there remains a need for anti-biofouling compounds possessing significant topological and chemical heterogeneity.

SUMMARY

The disclosed subject matter provides terpolymers of hyperbranched fluoropolymers, PEG and PDMS to mitigate biofouling in various applications. In accordance with one aspect of the disclosed subject matter, a compound of Formula A as illustrated and below is provided:

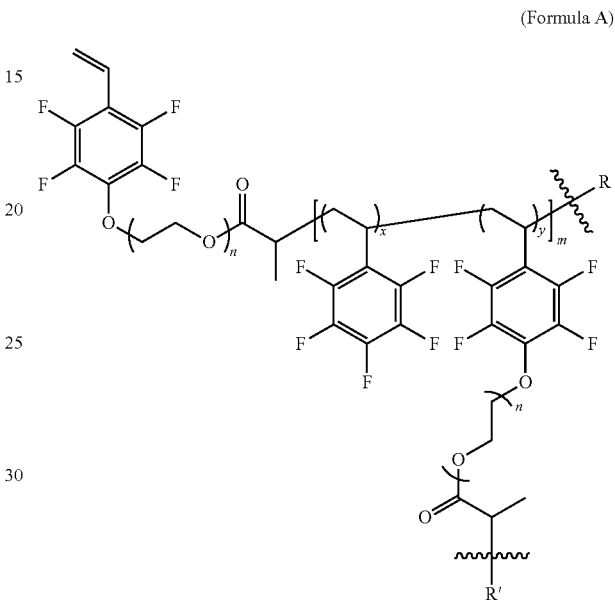

(Formula A)

wherein:
n is selected from an integer between 1 and 15 inclusive;
x is selected from a number between 0.01 and 0.99, where y=(1−x);
m is selected from an integer between 1 and 250 inclusive;
R is selected from the group consisting of

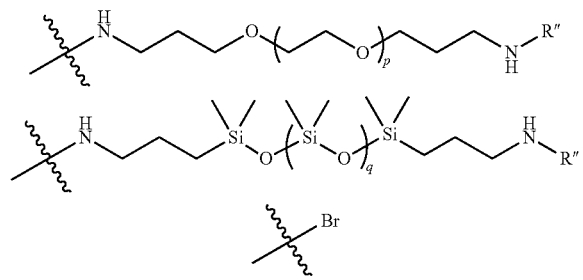

and R' is selected from the group consisting of

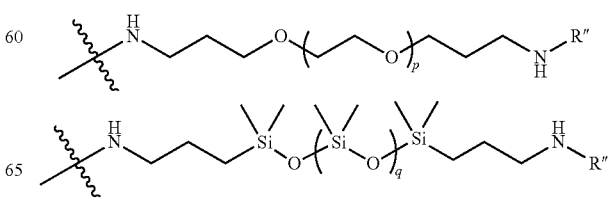

wherein p and q are integers independently selected from between 1 and 250 inclusive and R" is another domain of Formula A or Hydrogen.

According to certain embodiments of the disclosed subject matter, the compound of Formula A is represented by Compound Q, which is defined to have the formula of FIG. 21, wherein n is selected from an integer between 1 and 15 inclusive, and p and q are independently selected from an integer between 1 and 250 inclusive.

According to another aspect of the disclosed subject matter, a method for reducing biofouling of a surface is provided. The method includes providing a terpolymer according to Formula A above to a surface susceptible to biofouling.

According to another aspect of the disclosed subject matter, a method for preparing a compound for reducing fouling of a crude hydrocarbon in a hydrocarbon refining process is provided. The method includes:

(a) reacting 2,3,4,5,6-pentafluorostyrene with polyethylene glycol to obtain a product represented by Formula I below:

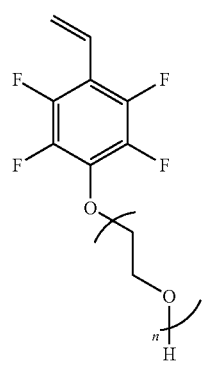

(I)

wherein n is selected from an integer between 1 and 15 inclusive;

(b) reacting the product obtained in (a) with 2-bromopropionyl bromide to obtain a product represented by Formula II below:

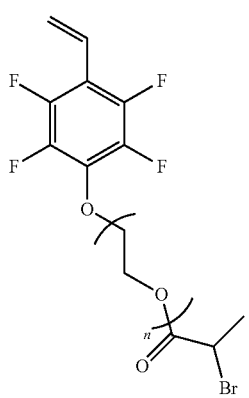

(II)

(c) reacting the product obtained in (b) with 2,3,4,5,6-pentafluorostyrene to obtain a branched fluoropolymer represented by Formula III

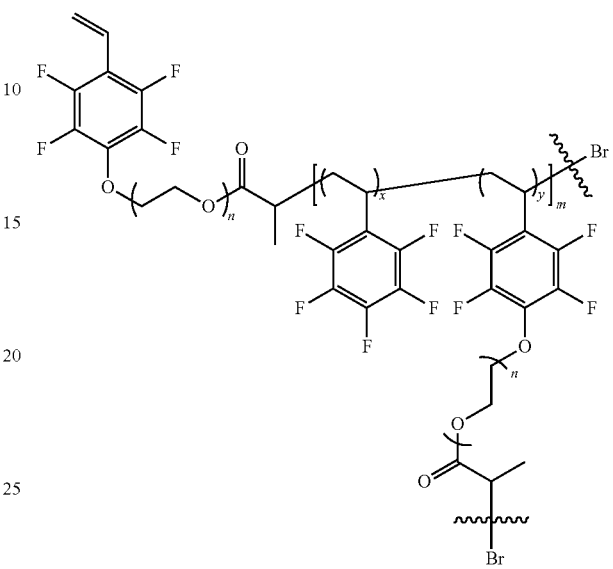

(III)

below:
wherein n is selected from an integer between 1 and 15 inclusive;
x is selected from a number between 0.01 and 0.99, where y=(1−x); and m, q, and p are independently selected from an integer between 1 and 250 inclusive; and (d) reacting the branched fluoropolymer obtained in (c) with chain bisaminopropyl-polyethylene glycol having between 1 and 250 monomer units and bisaminopropyl-polydimethylsiloxane having between 1 and 250 monomer units to obtain a terpolymer of the branched fluoropolymer, polyethylene glycol and polydimethylsiloxane.

According to a further aspect of the disclosed subject matter, a compound prepared by the above method is provided.

According to another aspect of the disclosed subject matter, a method for mitigating biofouling of a surface is provided. The method includes providing a surface susceptible to biofouling and contacting the surface with a compound represented by Formula A. According to a further aspect of the disclosed subject matter, a composition comprising Formula for mitigating biofouling of a surface is provided.

In addition, the disclosed subject matter provides compositions comprising the compound identified above, and products incorporating compositions comprising the compound identified above.

BRIEF DESCRIPTION OF THE DRAWINGS

The disclosed subject matter will now be described in conjunction with the accompanying drawings in which:

FIG. 4A is a contour graph of static water contact angle measurement of a dry film. FIG. 4B is a contour graph of static water contact angle measurement on a water-saturated film.

FIG. 6A is an AFM micrograph of the topography of the HBFP-PEG-PDMS terpolymer network (4 µm$^2$ field of view). FIG. 6B is a surface force spectroscopy map of surface modulus of the HBFP-PEG-PDMS terpolymer network, with relative modulus superimposed over network topography in perspective view. FIG. 6C is a surface force spectroscopy map of deformation of the HBFP-PEG-PDMS terpolymer network, with deformation superimposed over a three-dimensional rendering of network topography in perspective view. FIG. 6D is a surface force spectroscopy map of relative adhesion force of the HBFP-PEG-PDMS terpolymer network, with relative adhesion force superimposed over a three-dimensional rendering of network topography in perspective view. FIG. 6E is a surface force spectroscopy map of relative dissipation of the HBFP-PEG-PDMS terpolymer network, with relative dissipation superimposed over a three-dimensional rendering of network topography in perspective view.

FIG. 11A is a graph of storage modulus and temperature vs. time; FIG. 11B is a graph of loss modulus and tan δ vs. time; and FIG. 11C is a graph of total change in modulus per unit change in temperature v. temperature.

FIG. 13A is an illustration of fluorescence signal intensities before and after BSA incubation. FIG. 13B is a representative confocal photomicrograph for a PDMS standard network. FIG. 13C is a representative confocal photomicrograph for a HBFP-PEG-PDMS terpolymer network.

DETAILED DESCRIPTION

Definitions

The following definitions are provided for purpose of illustration and not limitation.

As used herein, the term "biofouling" generally refers to the accumulation of undesired organisms, microorganisms, and proteins on surfaces exposed to environments where microorgansisms and organisms reside.

As used herein, the term "surface susceptible to biofouling" generally refers to any surface exposed or potentially exposed to an environment where microorganisms and organisms reside, and refers to both internal and external surfaces so exposed.

As used herein, mitigation of biofouling is generally achieved when the susceptibility of a surface to microorganism, organism and/or protein adhesion is reduced, or when the force required to remove adhered microorganisms, organisms and/or proteins is reduced, or when the overall degree of biofouling observed for a surface is reduced relative to a similar surface in a similar environment.

As used herein, reference to a group being a particular polymer (e.g., polyethylene glycol or polydimethylsiloxane) encompasses polymers that contain primarily the respective monomer along with negligible amounts of other substitutions and/or interruptions along polymer chain. In other words, reference to a group being a polyethylene glycol group does not require that the group consist of 100% ethylene glycol monomers without any linking groups, substitutions, impurities or other substituents (e.g., alkylene substituents). Such impurities or other substituents can be present in relatively minor amounts so long as they do not affect the functional performance of the compound, as compared to the same compound containing the respective polymer substituent with 100% purity.

As used herein, a terpolymer is a polymer comprising at least three different polymer substitutents (such as PEG, PDMS, and HBFP).

Reference will now be made to various aspects of the disclosed subject matter in view of the definitions above.

Figure 22:
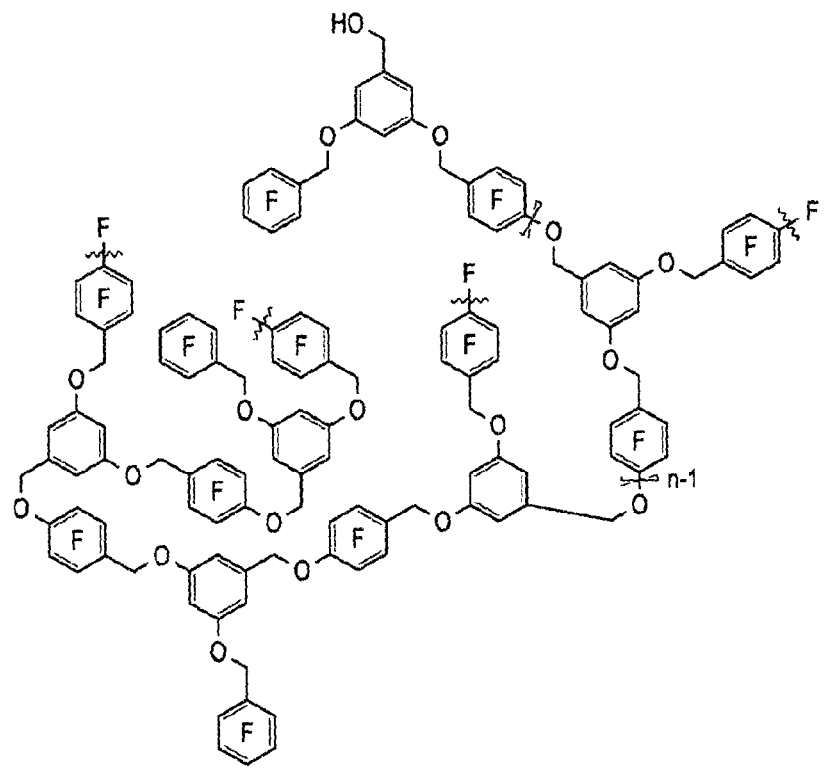
FIG. 22 is the structural chemical formula of HBFP(I).
Figure 23:
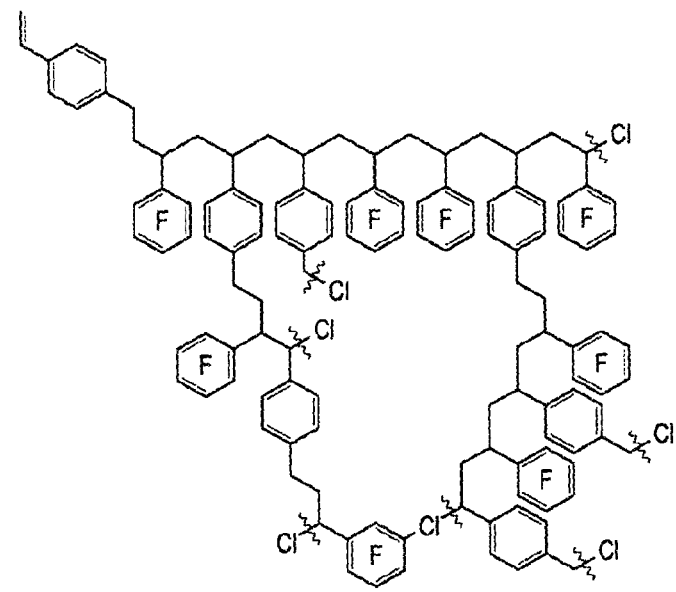
FIG. 23 is the structural chemical formula of HBFP(II)
Figure 24:
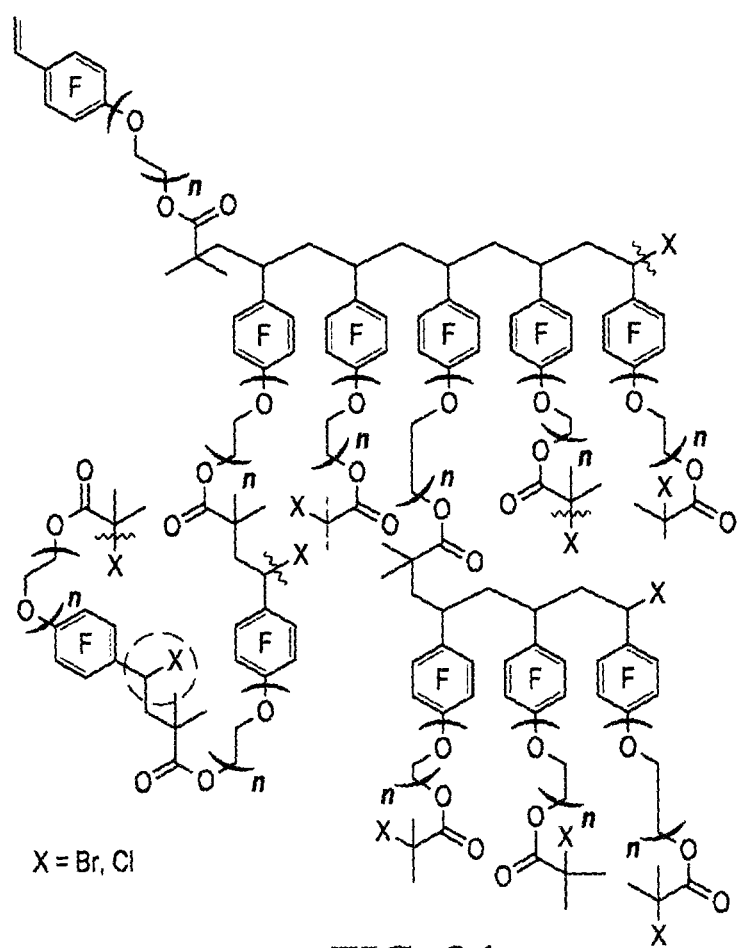
FIG. 24 is the structural chemical formula of HBFP(III).
Figure 25:
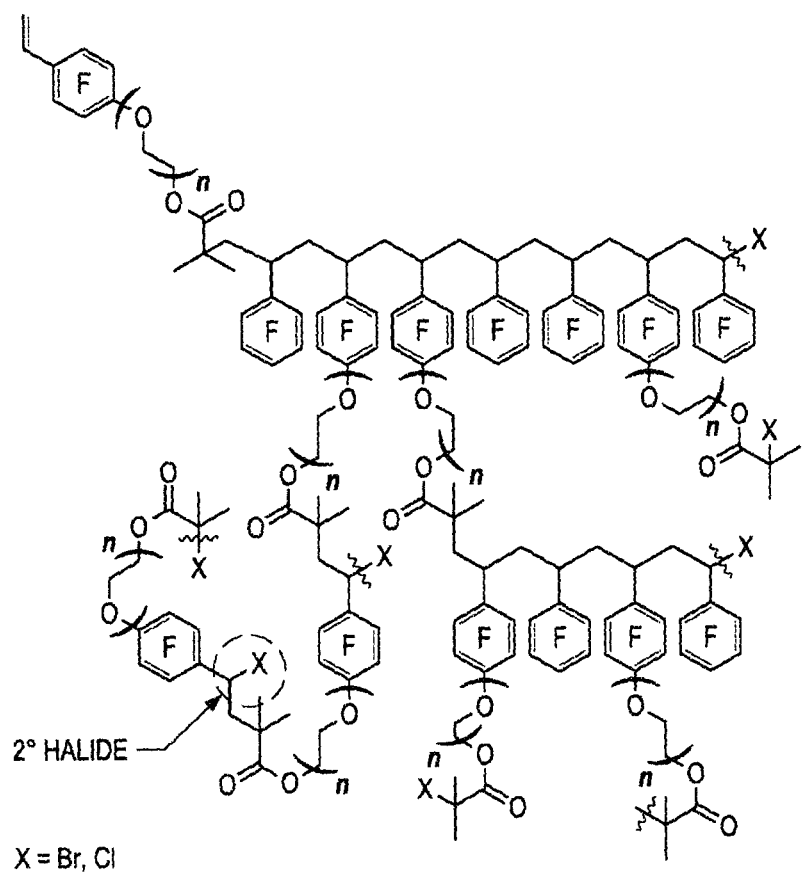
FIG. 25 is the structural chemical formula of HBFP(IV).

In accordance with another aspect of the disclosed subject matter, a terpolymer comprising a hyperbranched fluropolymer is provided. Suitable HBFPs include, but are not limited to, HBFP(I) (FIG. 21), HBFP(II) (FIG. 22), HBFP(III) (FIG. 23), and HBFP(IV) (FIG. 24) and derivatives thereof.

Such HBFPs may be synthesized using methods known in the art. See Bartels, J. W.; Cheng, C.; Powell, K. T.; Xu, J.; Wooley, K. L. *Macromol. Chem. Phys.* 2007, 208, 1676, the disclosure of which is incorporated by reference.

Suitable hydrophilic polymer components can be of neutral, anionic, cationic or zwitterionic charge character, and include, for example, PEG and PEG derivatives (e.g., bisamino-propyl PEG), poly(N-vinylpyrolidinone), polyacrylamide, poly(acrylic acid), polyethyleneimine, polycarboxybetaine, polysulfobetaine, and derivatives thereof.

Hydrophilic polymers have an affinity for water, as measured by a low water contact angle (<30°), and/or swellability or solubility in water. The amount of hydrophilic polymer component may vary. For example, the hydrophobic component may vary between 0-75 wt %, calculated with respect to the weight of the HBFP-containing component. The hydrophilic polymer component may be linear or branched.

Suitable hydrophobic polymer components include, for example, PDMS and PDMS derivatives (e.g., bisamino-propyl PDMS), polyisoprene, Bolton hyperbranched polyesters, poly(methyl (meth)acrylate), polystyrene, and derivatives thereof. Hydrophobic polymers lack an affinity for water, as measured by a high water contact angle (>90°). The amount of hydrophobic components may vary. For example, the hydrophobic polymer component may vary between 0-75 wt %, calculated with respect to the weight of the HBFP-containing component. The hydrophobic polymer component may be linear or branched.

The hydrophilic components and hydrophobic components form crosslinks with the HBFP-containing components. Such crosslinking provides a three-dimensional network from the otherwise low-viscosity, HBFP. The crosslinking with either hydrophilic or hydrophobic components creates an amphiphilic coating possessing chemical and surface heterogeneity on both the nano- and micro-scales. In certain embodiments, crosslinks may form via a substitution reaction of the bromoacetyl and bromobenzyl groups of HBFP with the amine termini of both the linear PEG and PDMS crosslinkers and crosslinking may be affected through a deposition followed by a thermal curing. In other embodiments, photo-chemically-initiated thiol-ene reactions or other typical chemical reactions are used to form the crosslinks, for suitably-functionalized HBFP, hydrophilic and hydrophobic polymer components.

In one aspect of the disclosed subject matter, the present disclosure provides compositions comprising the reaction product of a hyperbranched fluoropolymer (HBFP)-containing component, a hydrophilic polymer component, and a hydrophobic polymer component.

In accordance with certain embodiments of the disclosed subject matter, In accordance with one aspect of the disclosed subject matter, a compound of Formula A as illustrated and below is provided:

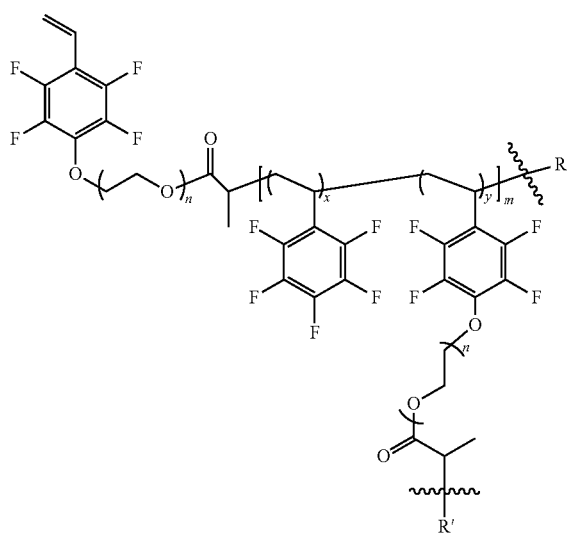

(Formula A)

wherein:

n is selected from an integer between 1 and 15 inclusive;

x is selected from a number between 0.01 and 0.99, where $y=(1-x)$;

m is selected from an integer between 1 and 250 inclusive;

R is selected from the group consisting of

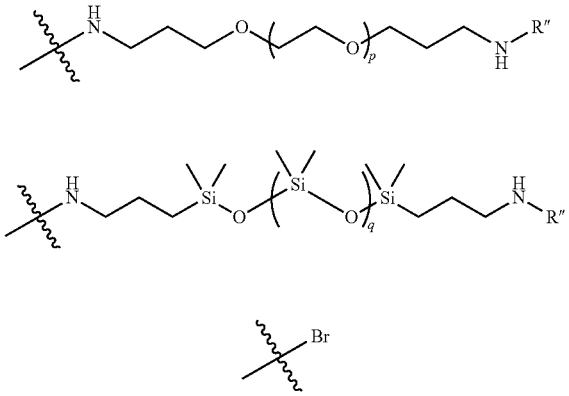

and R' is selected from the group consisting of

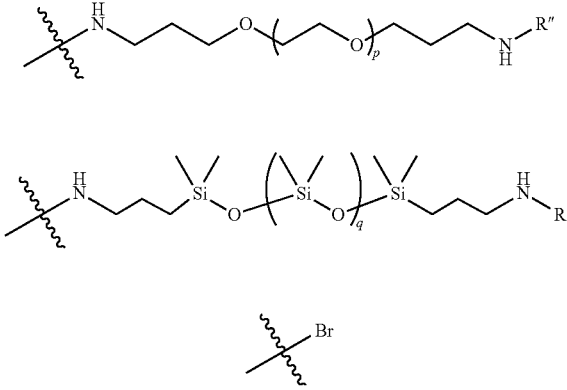

wherein p and q are integers independently selected from between 1 and 250 inclusive and R" is another domain of Formula A or Hydrogen.

Figure 21:
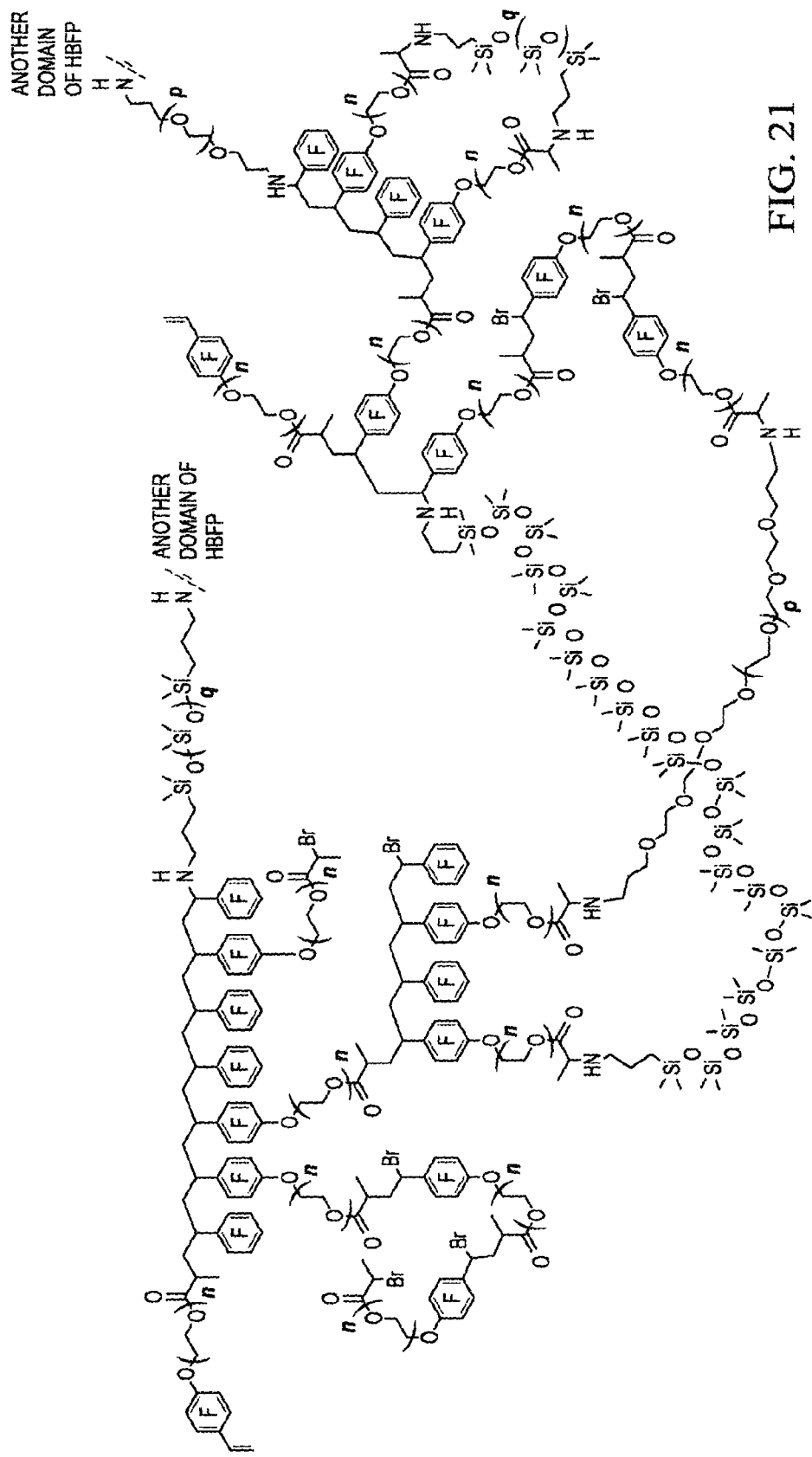
FIG. 21 is the structural chemical formula of Compound Q.

According to certain embodiments of the disclosed subject matter, the compound of Formula A is represented by Compound Q, which is defined to have the formula of FIG. 21, wherein n is selected from an integer between 1 and 15 inclusive, and p and q are independently selected from an integer between 1 and 250 inclusive.

According to another aspect of the disclosed subject matter, a method for reducing biofouling of a surface is provided. The method includes providing a terpolymer according to Formula A above to a surface susceptible to biofouling.

According to another aspect of the disclosed subject matter, a method for preparing a compound for mitigating biofouling is provided. The method includes:

(a) reacting 2,3,4,5,6-pentafluorostyrene with polyethylene glycol to obtain a product represented by Formula I below:

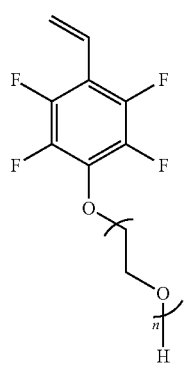

(I)

wherein n is selected from an integer between 1 and 15 inclusive;

(b) reacting the product obtained in (a) with 2-bromopropionyl bromide to obtain a product represented by Formula II below:

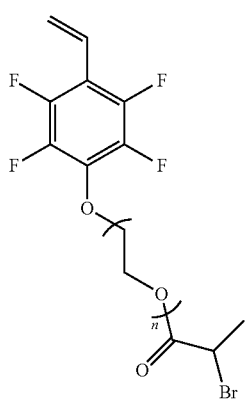

(II)

(c) reacting the product obtained in (b) with 2,3,4,5,6-pentafluorostyrene to obtain a branched fluoropolymer represented by Formula III below:

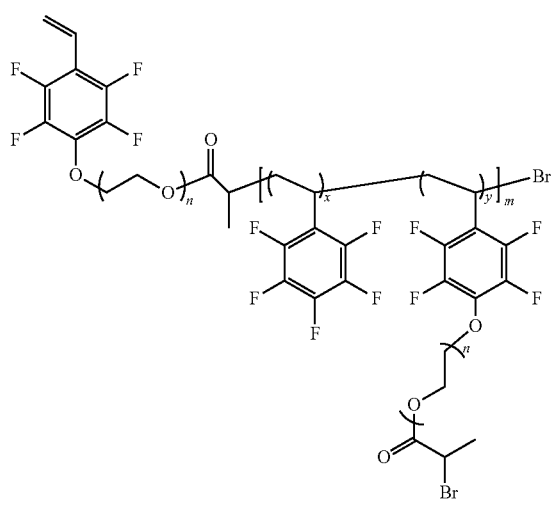

(III)

where n can be selected from an integer between 1 and 15 inclusive, x can be selected from a number between 0.01 and 0.99, and y=(1−x), and m, q, and p can be independently selected from an integer between 1 and 250 inclusive, and (d) reacting the branched fluoropolymer obtained in (c) with chain bisaminopropyl-polyethylene glycol having between 1 and 250 monomer units and bisaminopropyl-polydimethylsiloxane having between 1 and 250 monomer units to obtain a terpolymer of the branched fluoropolymer, polyethylene glycol and polydimethylsiloxane.

In certain embodiments, the HBFP precursor can be generated by nucleophilic aromatic substitution of 2,3,4,5,6-pentafluorostyrene with excess polyethylene glycol in the presence of sodium hydride and tetrahyrofuran at 0 degrees Celsius followed by maintenance at room temperature in a nitrogen gas atmosphere for 14 hours, as shown in reaction scheme 1 below.

Reaction Scheme 1

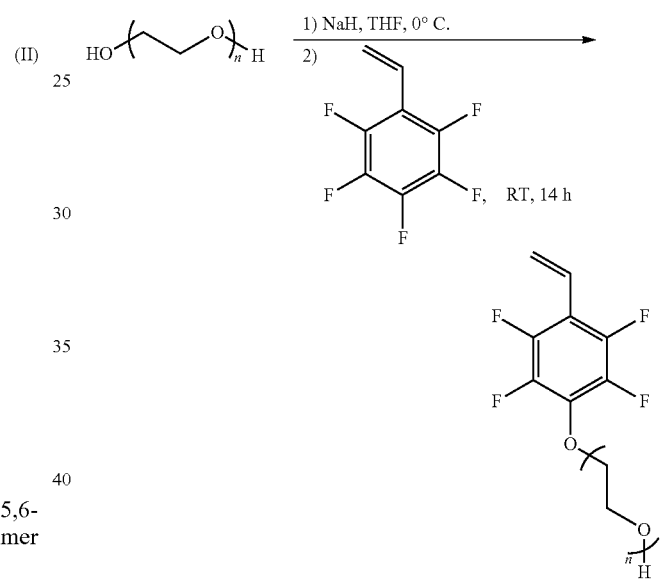

Subsequently, the product of scheme one can be esterified by reaction with 2-bromopropionyl bromide in triethylamine and tetrahydrofuran at 0 degrees Celsius followed by stirring at room temperature for 16 hours in a nitrogen gas atmosphere, as shown in scheme 2 below.

Reaction Scheme 2

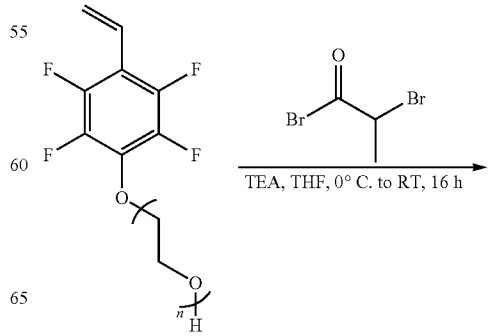

-continued

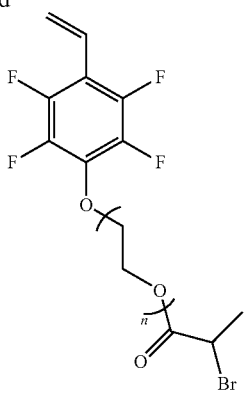

Subsequently, the inimer product of Reaction Scheme 2 can be copolymerized via CuBr and PMDETA catalysis to promote atom transfer radical condensation vinyl copolymerization to generate HBFP as shown in Reaction Scheme 3 below.

Figure 26:
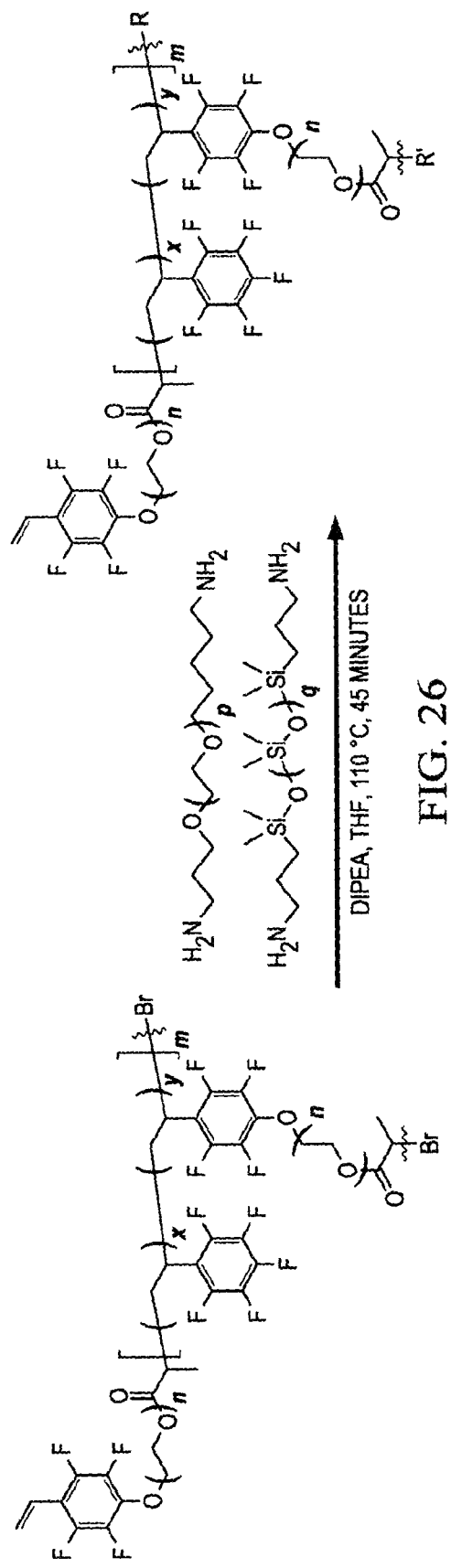
FIG. 26 is the structural chemical formulas of Reaction Scheme 4.

The HBFP product of Reaction Scheme 3 can subsequently be crosslinked with bis(3-aminopropyl)-terminated PEG and bis(3-aminopropyl-terminated PDMS via Reaction Scheme 4 shown in FIG. 26.

The reactions of Reaction Scheme 4 above can be performed by deposition and curing of the HBFP with the PEG and PDMS substrates in the presence of base to yield robust free-standing films.

In some embodiments according to the disclosed subject matter, the weight percent of the PEG in the terpolymer can be between about 0.5% and about 99% of the total weight of the terpolymer compound. In additional embodiments, the weight percent of polyethylene glycol relative to the terpolymer is between about 10% and about 90%, and in still further embodiments, the weight percent is between about 15% and about 35%.

In additional embodiments according to the disclosed subject matter, the weight percent of the PDMS can be between about 0.5% and about 99% of the total weight of the terpolymer compound. In additional embodiments, the weight percent of polyethylene glycol relative to the terpolymer is Reaction Scheme 3

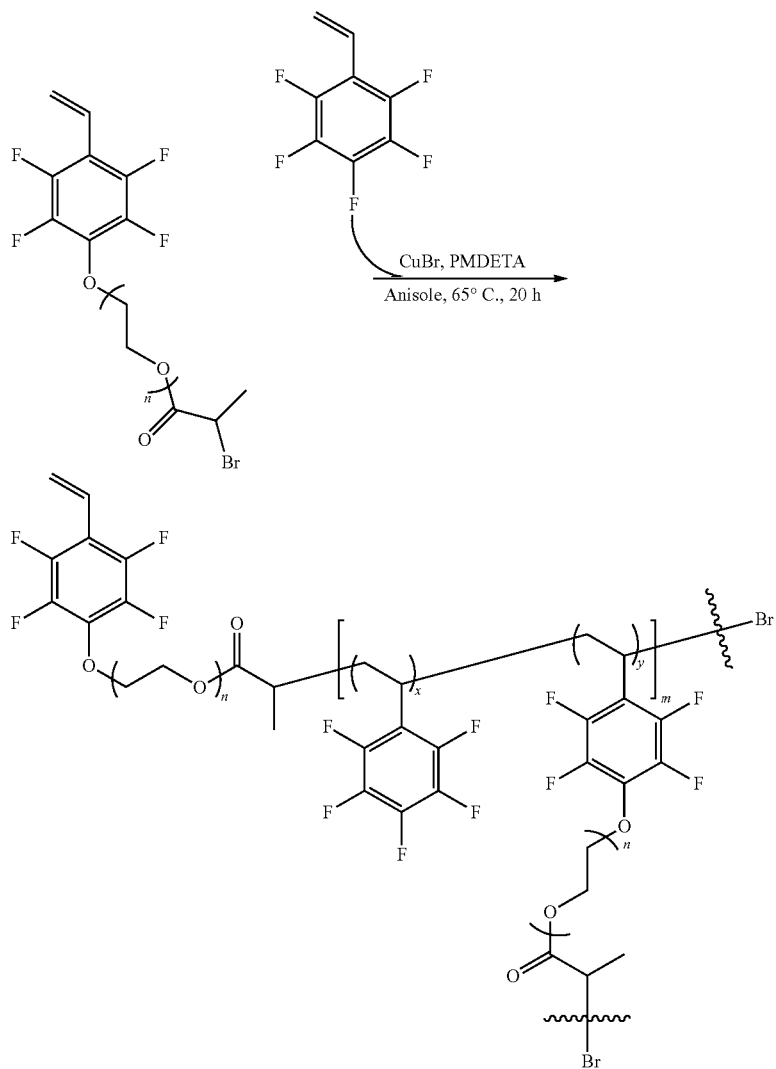

between about 10% and about 90%, and in still further embodiments, the weight percent is between about 15% and about 35%.

Topological Heterogeneity of HBFP-PEG-PDMS Terpolymers

In certain embodiments, the HBFP-PEG-PDMS terpolymers of the present disclosure can be characterized by a heterogeneous distribution of chemical domains. For example, certain HBFP-PEG-PDMS terpolymers display heterogenous, patch-work patterns of hydrophobic (e.g., low surface energy) and hydrophilic (e.g., water soluble and swellable) domains. The combination of hydrophobic, or rigid, domains with hydrophilic, or dynamic, domains provides a material capable of, among other things, reducing or preventing biofouling, and/or promoting foulant release and removal. In other examples, certain HBFP-PEG-PDMSs may be characterized by increased fluorine content at the surface of the material.

In certain embodiments, the HBFP-PEG-PDMS of the present disclosure may be characterized by a micro- and nanoscopically-resolved topography. Topographical heterogeneity at the nanoscale may, among other things, prevent or reduce protein and/or polysaccharide adhesion. Topographical heterogeneity at the microscale may, among other things, prevent or reduce organism adhesion. Together nano- and microscale topographical heterogeneity may synergistically work to prevent biofouling.

In certain embodiments, the HBFP-PEG-PDMS of the present disclosure may be characterized by a heterogeneous distribution of structural domains. For example, certain HBFP-PEG-PDMSs display heterogeneous, patch-work patterns of hydrophobic (e.g., rigid or hard) and hydrophilic (e.g., soft, dynamic or swellable) domains. The combination of domains with these properties provides a material capable of, among other things, reducing or preventing biofouling. In certain embodiments, the HBFP-PEG-PDMS of the present disclosure may show dynamic surface reorganization upon immersion in water, as measured by static water contact angle.

In certain embodiments, the HBFP-PEG-PDMS of the present disclosure may comprise a raised region, wherein the raised region is characterized by a high modulus, a low deformation, a low surface energy, and low dissipation; a lattice region, wherein the lattice region is characterized by a moderate modulus, a moderate deformation, a low surface energy, and a moderate dissipation; and a deeper interstitial region, wherein the deeper interstitial region is characterized by a low modulus, a high deformation, a high surface energy, and a high dissipation.

The dynamic and heterogeneous topology of the disclosed compounds has significant functional consequences in biofouling mitigation applications. Any fouling that occurs upon a substrate involves balancing of particular molecular-level attractive and repulsive interactions between the foulant and the surface. Marine organisms initially probe surfaces, decide whether or not to settle on either a hydrophobic, hydrophilic, soft or hard substrate and adhere by the secretion of adhesin proteins. In biomedical applications of materials, many different types of biomolecules and biomacromolecules make contact with the substrate, depending on the particular mechanism and site of administration. In other applications of anti-fouling coatings, the foulants may be various biological or synthetic chemicals encountered in the environment. Different fouling species experience different binding interactions with different anti-fouling coatings components. By designing polymer networks that present compositionally, topographically and morphologically-heterogeneous surfaces, therefore, a complex profile of attractive and repulsive interactions is provided, to limit the dimensions over which adhesion may occur. Moreover, the characteristic of dynamic reorganization of the surface components is a mechanism by which to alter the composition, topography, morphology features that are presented from the surface and, thereby, detach any initially adhered species, or to intercept and prevent their adhesion before it occurs. The combination of a complex surface that is capable of in situ reorganization is a powerful and unique concept toward anti-fouling coatings that exhibit exceptional anti-foulant and foulant-releasing performance.

As disclosed herein, and with reference to Example 1 below, the various topographical characterizations of the embodiments disclosed herein support a varied and dynamic topology for biofouling mitigation applications. For example, static surface contact angle measurements before and after water equilibration of these ternary systems provide compelling evidence of dynamic reordering in these systems. Further, by varying the formulation (e.g. PDMS and PEG ratios to HBFP), the system can be tailored to express greater amounts of hydrophobicity or hydrophilicity on exposure to water and sea water. These reordering events are indicative of a non-static surface that contributes to greater heterogeneity in a dynamic fashion, in addition to its intrinsic heterogeneity as cast, and is intended to further confuse and dissuade biologic entities for settling.

Additionally, environmental dynamic mechanical analysis (DMA) shows the bulk effects of the system in submersion at in-ocean and in-body conditions by exposing the system to temperatures and solvents that are similar to the environments of both applications. While the kinetics of the mechanical response to solvation, swell and the onset of a solvated steady-state response are obtainable from such studies, the determination of the final steady state behavior is perhaps most critical, as this will ultimately determine film wear and mechanical matching to any substrate. Moreover, Atomic force microscopy (AFM) and surface force spectroscopy (SFS) explicitly show both topographic complexity on the nano and microscale, while also capturing the exact distribution of constituents at the surface by relating nanomechanical measurements to the known behavior of PEG, PDMS and HBFP.

Uses of the Additives and Compositions for Antifouling Applications

The additives of the disclosed subject matter can be used in compositions that mitigate biofouling. For purpose of example and not limitation, suitable compositions for the disclosed compounds include surface coatings, including anti-fouling coatings for any surface that is placed in contact with a marine environment, biological fluid, or the environment. For purpose of example and not limitation, the disclosed compounds are suitable for coatings for maritime vessels, undersea cables, lenses for sonar and other instruments, glass or plastic windows, solar panels, food packaging materials, catheters, i.v. needles, medical implants, stents, heart valves, pacemakers, pacemaker wires, and any other body-implantable device. In addition to the additives of the disclosed subject matter, the compositions can further contain adhesion agents, such as epoxides, dispersants, and stabilizers.

The compositions of the disclosed subject matter can further include, for example, lubricants, corrosion inhibitors, and reduced-friction surface coatings.

Furthermore, the additives of the disclosed subject matter can be added with other compatible components that address other problems that can present themselves in an oil refining process known to one of ordinary skill in the art.

The compounds of the disclosed subject matter can be incorporated into surface coatings and surface adhesives for disposition over the surface of an article. According to one aspect of the disclosed subject matter, the compounds are applied by means of dropping, painting, or pouring a solution containing the compounds onto the surface. Additionally or alternatively, and with reference to Example 2 below, the compounds can be spray coated over the surface of an article susceptible to biofouling. Coatings incorporating the disclosed compounds can be applied before first exposure of a surface to biofouling or during the life of the surface after initial exposure to biofouling.

While not limited thereto, the compounds of the disclosed subject matter are particularly suitable in reducing or preventing biofouling fouling. Thus one aspect of the disclosed subject matter provides a method of reducing and/or preventing, in particular, biofouling that includes adding at least one compound of the disclosed subject matter to a surface that is known to or believed to be susceptible to biofouling.

In some embodiments of the disclosed subject matter, a method to mitigate biofouling is provided comprising adding any one of the above-mentioned compounds to a coating for a surface that is susceptible to biofouling.

The total amount of the compound to be added to a coating or applied directly to a surface can be determined by a person of ordinary skill in the art. In one embodiment, substantially the entire surface susceptible to biofouling is coated with the compound.

The compounds of the disclosed subject matter can be added to a coating solution in a solid (e.g. powder or granules) or liquid form directly to the coating solution. Any suitable technique can be used for adding the compound to a coating solution, as known by a person of ordinary skill in the art in view of the process to which it is employed.

EXAMPLES

The disclosed subject matter is further described by means of the examples, presented below. The use of such examples is illustrative only and in no way limits the scope and meaning of the disclosed subject matter or of any exemplified term. Likewise, the disclosed subject matter is not limited to any particular preferred embodiments described herein. Indeed, many modifications and variations of the disclosed embodiments will be apparent to those skilled in the art upon reading this specification.

Example 1

Synthesis and Characterization of HFBP-PEG-PDMS Terpolymer

Materials

Reagents were purchased from Sigma Aldrich and used as received unless otherwise noted. 2,3,4,5,6-Pentafluorostyrene (PFS) was purchased from Apollo Scientific (UK) and filtered through a plug of neutral alumina prior to use. 2,4,6-tris(bromomethyl)mesitylene was purchased from Combi-Blocks. Sylgard 184 elastomer was purchased from Dow Corning and prepared according to their protocol. Bovine serum albumin (BSA) conjugated to Alexa Fluor 680 was purchased from Invitrogen. Sylgard 184 (Dow Corning) was purchased from Ellsworth Adhesives and was prepared as instructed.

Nuclear Magnetic Resonance Spectroscopy and Mass Spectrometry

Monomers and polymers were characterized by $^1$H, $^{13}$C and $^{19}$F nuclear magnetic resonance (NMR) spectroscopies using a Varian Inova 300 spectrometer. $^1$H and $^{13}$C NMR spectra were analyzed using the solvent signal as an internal reference and $^{19}$F NMR spectra were analyzed with $CF_3COOH$ as an external standard. High-resolution mass spectrometry (HRMS) for the monomers was conducted on an Applied Biosystems PE SCIEX QSTAR. Spectral data for the small molecules are reported elsewhere.

Infrared and X-Ray Photoelectron Spectroscopy

IR spectra were obtained on a Shimadzu IR Prestige attenuated total reflectance Fourier-transform infrared spectrometer (ATR-IR). Spectra were analyzed using IRsolution software package (Shimadzu). X-ray photoelectron spectroscopy (XPS) measurements were taken with a Kratos Axis Ultra Imaging X-ray photoelectron spectrometer, using Mono A1 anode, 12 kV voltage and 10 mA current.

Gel Permeation Chromatography

Gel permeation chromatography was performed on a Waters Chromatography, Inc. (Milford, Mass.), 1515 isocratic HPLC pump equipped with an inline degasser, a model PD2020 dual-angle (15° and 90°) light scattering detector (Precision Detectors, Inc.), a model 2414 differential refractometer (Waters, Inc.), and four $PL_{gel}$ polystyrene-co-divinyl-benzene gel columns (Polymer Laboratories, Inc.) connected in series: 5 μm Guard (50×7.5 mm), 5 μm Mixed C (300×7.5 mm), 5 μm $10^4$ (300×7.5 mm), and 5 μm 500 Å (300×7.5 mm) using the Breeze (version 3.30, Waters, Inc.) software.

Elemental Analysis

Elemental analysis of the polymers was performed at Midwest Microlab, LLC (Indianapolis, Ind.).

Thermal Analysis

Differential scanning calorimetric (DSC) studies were performed on a Mettler-Toledo $DSC822^e$ (Mettler-Toledo, Inc., Columbus, Ohio), with a heating rate of 10° C./min. The $T_g$ was taken as the midpoint of the inflection tangent, upon the third heating scan. Thermogravimetric analysis was performed under Ar atmosphere using a Mettler-Toledo model TGA/DSC 1 $Star^e$ system, with a heating rate of 10° C./min. Measurements were analyzed using Mettler-Toledo Star software version 10.00d.

Atomic Force Microscopy and Surface Force Spectral Mapping

Atomic force microscopy was performed under ambient conditions in air. The AFM instrumentation consisted of a MFP-3D-BIO AFM (Asylum Research; Santa Barbara, Calif.) and standard silicon tips (type, OTESPA-70; L, 160 μm; normal spring constant, 50 N/m; resonance frequency, 246-282 kHz). Force spectroscopy mapping was performed via AFM measurements using a Bruker Multimode 8 system in PeakForce™ tapping mode. This imaging method also provides direct surface maps of modulus, dispersion, deformation and adhesion. In brief, the PeakForce™ QNM™ imaging mode uses a modified Hertzian model, the DMT model, to directly extract a reduced Young's modulus ($E_r$). The DMT model takes into account surface-tip interactions neglected in the Hertz model and also allows for mapping of adhesion force, deformation and dissipation energy.

In brief, the PeakForce™ QNM™ imaging mode that uses a modified Hertzian model, the $DMT^2$ model (equation 1), to directly extract a reduced Young's modulus ($E_r$). The DMT model takes into account surface-tip interactions neglected in the Hertz model.

$$E_r = \frac{3(F_T - F_a)}{4\sqrt{Rd^3}} \qquad (1)$$

In equation 1 for the DMT reduced Young's Modulus: $F_t$ is the force on the probe tip, $F_a$ is the adhesive force between the probe tip and the sample, R is the working tip radius, and d is the depth of surface deformation below the zero-force contact point. The reduced Young's modulus is related to the sample modulus by equation 2 and reduces to equation 3 where the modulus of the probe tip is much greater than the sample being measured.

$$\frac{1}{E_r} = \frac{(1-v^2)}{E} - \frac{(1-v_t^2)}{E_t} \quad (2)$$

$$\frac{1}{E_r} \approx \frac{(1-v^2)}{E} \quad (3)$$

This is where v is the sample Poisson's ratio, $v_t$ is the probe tip Poisson's ratio, $E_t$ is the probe tip modulus and E is the sample modulus. Force curve fitting after tip contact provides a reduced modulus value. The difference in force curve minima during approach and retraction provides adhesion force. The absolute minimum in tip Z position after contact dictates deformation. Finally, the hysteresis in the approach and retraction force curves provides dispersion values.

In these measurements, a ScanAsyst-Air (Bruker) with manufacturer specification for a spring constant of k=0.4 was used. For this study, no formal calibration was performed as the relative values for purposes of chemical identification were sought. Arbitrary values for tip size and the Poisson ratio were used. Thermal tuning of the cantilever gave a resonant frequency of 93 kHz. However, as PeakForce™ imaging uses the cantilever in an off-resonance mode of 2 kHz, this finding is not critical to the qualitative value of the imaging.

Mechanical Analysis

A Mettler Toledo TT-DMA system was used for all dynamic mechanical and dynamic thermal mechanical analysis (DMA/DTMA) studies. Submersion studies were performed in Hyclone (Thermo) calcium/magnesium free phosphate buffered saline solution (1X, PBS) for simulation of an in-vivo environment. Submersion studies were performed in synthetic sea water (Ricca Chemicals, cat. no. 8363-5, ASTM D 1141-substitute ocean water) for simulation of a marine environment. All measurements were taken in compression with a dynamic force of 0.1 N.

Static Surface Contact Angle

Contact angles were measured as static contact angles using the sessile drop technique with an Attension Theta optical tensiometer (Biolin Scientific). Drops were fitted with a Young-Laplace formula to calculate the static contact angle in the Theta software (Biolin Scientific).

Confocal Microscopy and Protein Adhesion Assay

Bovine serum albumin conjugated to AlexaFluor-680 (BSA) was dissolved in phosphate buffered saline (PBS) solution (pH 7.1) to a concentration of 0.1 mg/mL and stored in the dark. Sylgard 184 was used as a standard to test against the terpolymer film. The surface of the terpolymer network and Sylgard 184 were incubated in fresh PBS buffer for 10 min and dried via filtered nitrogen gas. The surfaces were then exposed to Alexa-Fluor-680 conjugate in PBS at 0.1 mg mL$^{-1}$ for 45 min in a dark chamber. After exposure, the surfaces were washed with 5 mL of PBS buffer and dried via filtered nitrogen gas for 1 h. Z-stacked confocal fluorescence images were taken of the BSA exposed surfaces and were discussed in terms of resultant intensity histograms. The imaging platform was a full spectral Olympus FV-1000 laser scanning confocal microscope operating with a 635 nm diode laser and fluorescence collection selected by a wide band monochrometer from 650 to 750 nm.

Synthesis

Hyperbranched Fluoropolymer (HBFP)

Figure 1:
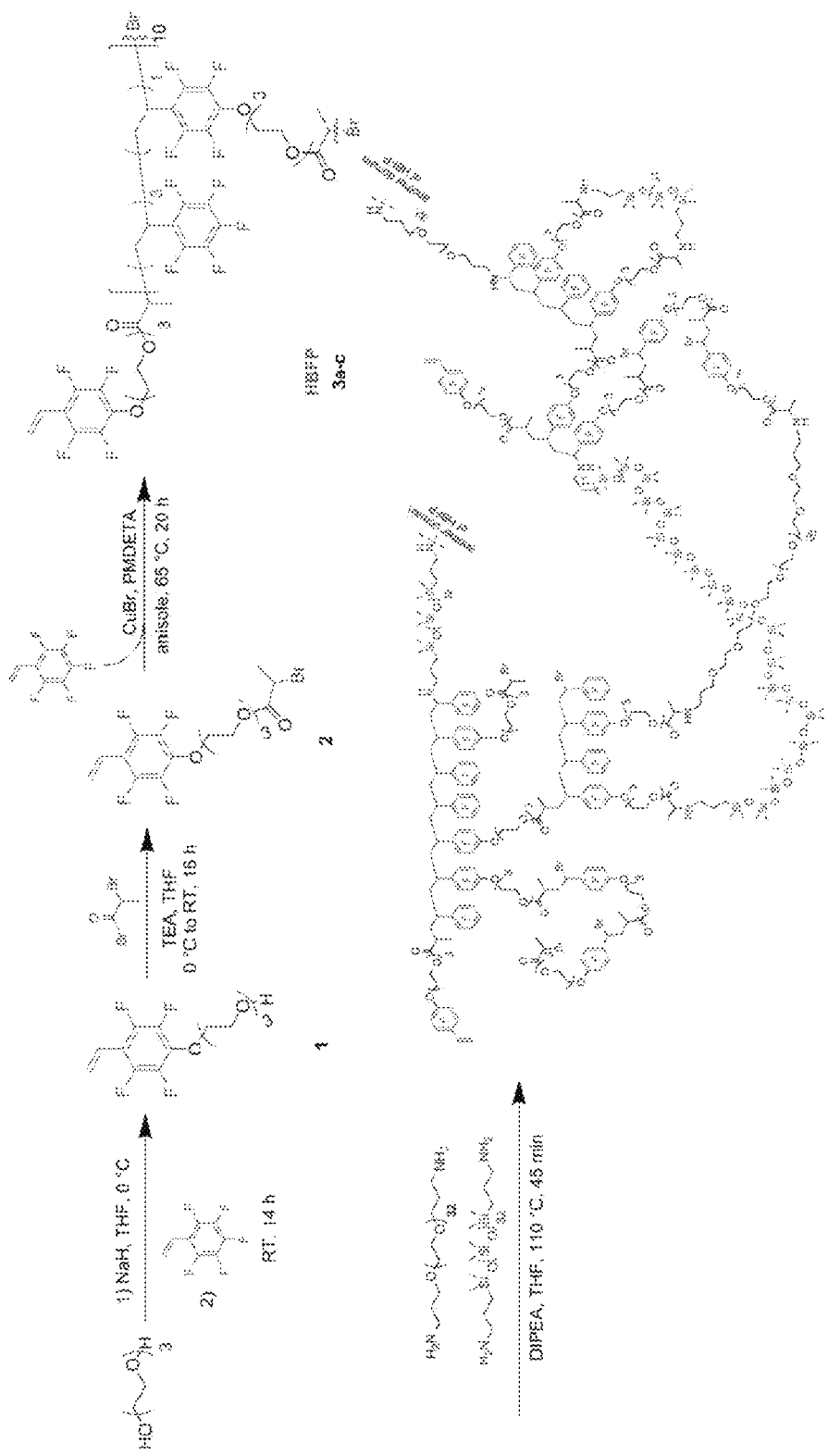
FIG. 1 is a schematic illustration of a synthesis protocol for a terpolymer of HBFP-PEG-PDMS.

The synthesis scheme is provided in FIG. 1, and further described below.

To a 250 mL Schlenk flask equipped with a stir bar was added 9.00 g (19.6 mmol) of compound 2 having the chemical structure below

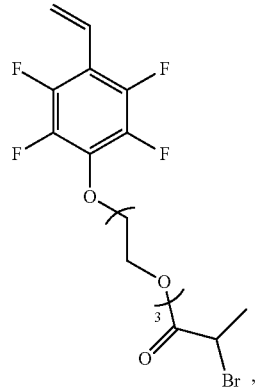

entafluorostyrene (PFS) (11.4 g, 58.8 mmol), pentamethyldiethylenetriamine (PMDETA) (8.18 mL, 39.2 mmol), CuBr (2.81 g, 10.9 mmol) and anisole (105 mL). The solution was deoxygenated via freeze-pump-thaw (×3), the vessel was backfilled with $N_2$ and then lowered into an oil bath set at 65° C. and the reaction was allowed to proceed for 26 h. The polymerization was quenched by opening the flask to air and submerging the flask in liquid nitrogen. Once thawed, the contents were dissolved in dichloromethane (500 mL), eluted through a plug of alumina to remove the catalyst, concentrated in vacuo, and the product was isolated by precipitation into cold hexanes (3×1.5 L) to afford a white powder of compound 3, having the chemical structure below:

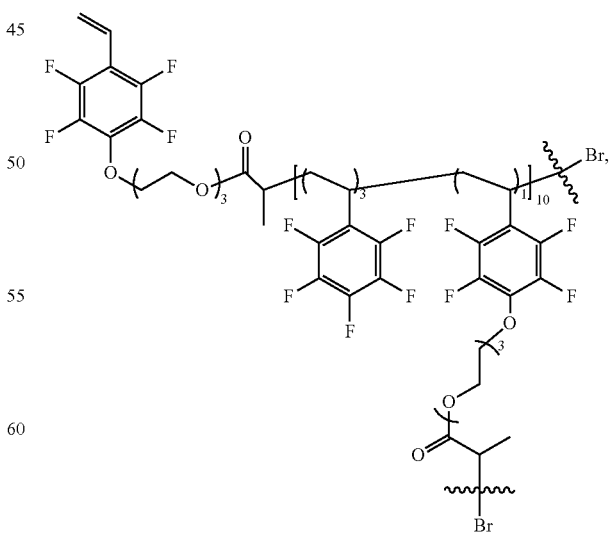

in 39% yield (7.80 g). IR=2947, 2878, 2361, 1744, 1651, 1497, 1296, 956 and 864 cm$^{-1}$. $^1$H NMR (CDCl$_3$, ppm): δ

0.7-1.5 (br m, C—CH$_3$), 1.5-3.1 (br m, CH$_2$—CH(R)-backbone), 3.4-4.0 (br m, R—O—CH$_2$—CH$_2$—OR'), 4.0-4.6 (br m, TFS-O—CH$_2$—CH$_2$—OR and R—CH$_2$—CH$_2$—O(O)C—R') ppm. $^{13}$C-NMR (CDCl$_3$, ppm): δ 24.7, 30.7-29.7, 32.1-41.7, 63.6, 68.8, 70.0-70.8, 74.3, 114.7, 122.2, 137.6, 140.7, 144.7, 176.6 ppm. $^{19}$F NMR (CDCl$_3$, ppm): δ −143 (br m, o-F (PFS) and o-F (TFS)), −157 (br m, p-F (PFS) and m-F (TFS)), −162 (br m, m-F (PFS)) ppm. The polymerization was repeated to give several batches of HBFP: 3a $M_w^{GPC}$=17400 Da, $M_n^{GPC}$=8600 Da, $M_w/M_n$=1.72. $T_g$=53° C. $T_{decomp}$: 310° C., 85% mass loss @ 500° C. 3b $M_w^{GPC}$=20100 Da, $M_n^{GPC}$=11200 Da, $M_w/M_n$=1.79. $T_{g,1}$=43° C., $T_{g,2}$=115° C. $T_{decomp}$: 242° C., 75% mass loss @ 500° C. Anal. Calc. for C$_{455}$H$_{259}$Br$_7$F$_{238}$O$_{35}$: C, 48.8%; H, 2.33%; F, 40.3%; Br, 4.99%. Found: C, 42.04; H, 3.00; F, 25.02; Br, <0.10%. 3c $M_w^{GPC}$=19700 Da, $M_n^{GPC}$=13000 Da, $M_w/M_n$=1.46. $T_{g,1}$=66° C., $T_{g,2}$=115° C., $T_{decomp}$: 345° C., 62% mass loss @ 500° C. Anal. Calc. for C$_{534}$H$_{276}$Br$_6$F$_{294}$O$_{30}$: C, 49.3%; H, 2.14%; F, 42.3%; Br, 3.69%. Found: C, 51.05; H, 3.12; F, 32.12; Br, 0.159%. 3a was used for the initial AFM imaging and contact angle study, 3b was used for the AFM data compiled as described below and 3c was used for all other studies presented.

Design of the Hyperbranched Fluoropolymer-Poly(Ethylene Glycol)-Poly(Dimethylsiloxane) Crosslinked Terpolymer Network (HBFP-PEG-PDMS) Two-Dimensional Series A series of HBFP-PEG-PDMS networks was prepared with a constant wt % of HBFP (3b) and at varying wt % PEG (0-75 wt %, calculated with respect to the weight of HBFP) and PDMS (25-75 wt %, calculated with respect to the weight of HBFP) to investigate how the relative stoichiometry of the crosslinkers affected surface topography and hydrophilicity.

General Procedure for the Preparation of HBFP-PEG-PDMS Crosslinked Terpolymer Networks The following general procedure was followed for each sample, as defined here for the terpolymer network having 25 wt % of each PEG and PDMS. To a scintillation vial was added a selected HBFP (100 mg), 1500 Da bis(3-aminopropyl)-terminated PEG (25 mg, 0.017 mmol, 25 wt %), 1500 Da bis(3-aminopropyl)-terminated PDMS (25 mg, 0.010 mmol, 25 wt %), THF (2 mL) and N,N-diisopropylethylamine (DIPEA) (0.05 mL, 0.3 mmol) and the mixture was stirred magnetically until homogeneous. The solution was drop cast (0.5 mL per slide) onto pre-cleaned, pre-cut 1 cm$^2$ glass microscope slides. A period of ca. 30 min allowed for the solvent to evaporate, which afforded a thick pre-gel that was cured at 110° C. for 45 min under N$_2$ atmosphere to afford the dry coatings. The crosslinked networks were then submerged in nanopure water bath overnight prior to characterization.

Preparation of PEG Films for ATR-IR and Surface Force Spectral Mapping

To a scintillation vial was added bis(3-aminopropyl)-terminated PEG (100 mg, 0.067 mmol), 2,4,6-tris(bromomethyl)mesitylene (18 mg, 0.045 mmol) and THF (1 mL) and stirred until homogeneous. To the solution was added DIPEA (0.12 mL, 0.69 mmol) and stirred for 30 min. The solution was drop cast onto pre-cleaned, pre-cut 1 cm$^2$ glass cover slips. A period of ca. 30 min allowed for the solvent to evaporate, which afforded a thick pre-gel that was cured at 110° C. for 45 min under N$_2$ atmosphere to afford the dry coatings.

Preparation of PDMS Films for ATR-IR and Surface Force Spectral Mapping

To a scintillation vial was added bis(3-aminopropyl) terminated PDMS (130 mg, 0.046 mmol), 2,4,6-tris(bromomethyl)mesitylene (12 mg, 0.030 mmol) and THF (1 mL) and stirred until homogeneous. To the solution was added DIPEA (0.09 mL, 0.52 mmol) and stirred for 30 min. The solution was drop cast onto pre-cleaned, pre-cut 1 cm$^2$ glass cover slips. A period of ca. 30 min allowed for the solvent to evaporate which afforded a thick pre-gel that was cured at 110° C. for 45 min under N$_2$ atmosphere to afford the dry coatings.

Results and Discussion

Synthesis

Figure 2:
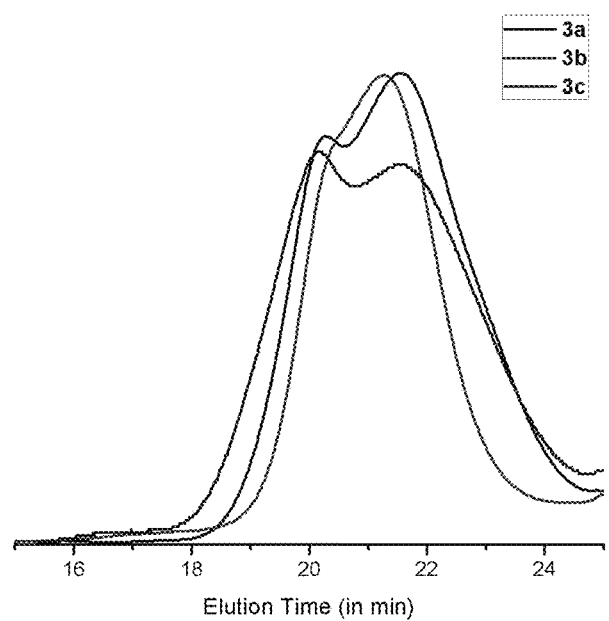
FIG. 2 illustrates gel permeation chromatography curves for the HBFPs as synthesized in Example 1.

A series of three HBFP-PDMS binary networks and nine HBFP-PEG-PDMS terpolymer networks was synthesized with varying stoichiometries of the HBFP, PEG (0, 25, 50 and 75 wt %, relative to HBFP) and PDMS (25, 50 and 75 wt %, relative to HBFP) components, to probe the compositional effects on the physical, mechanical and biological properties of the crosslinked materials. The process began through the generation of HBFP by synthesizing the precursor compound 1, having the chemical structure shown below,

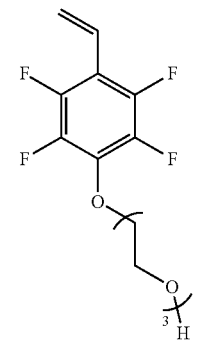

through a nucleophilic aromatic substitution of PFS with an excess of tri(ethylene glycol) followed by esterification of the remaining hydroxyl group by reaction with 2-bromopropionyl bromide to afford the inimer compound 2. Copolymerization of compound 2 with PFS using CuBr and PMDETA to facilitate atom transfer radical self-condensing vinyl copolymerization was conducted repeatedly to generate HBFP, 3a-c. As shown in FIG. 2, the three batches of HBFP were synthesized with only subtle differences in molecular weights, molecular weight distributions, and thermal properties. Because the three samples of HBFP were of similar composition, structure and size, each was able to be taken forward individually to create the series of crosslinked terpolymer networks with bis(3-aminopropyl)-terminated PEG and bis (3-aminopropyl)-terminated PDMS, while allowing for direct comparisons to be made regarding the effects of network composition. Significantly lower % Br contents vs. the theoretical values were measured by elemental analysis, which could be due to biradical coupling and/or elimination reactions during the copolymerization and is being studied in further detail. Nonetheless, stable networks were established, presumably through a crosslinking between the bromoacetyl and bromobenzyl functional handles of the HBFP with the terminal amines of the PEG and PDMS. The networks were generated through deposition along the surface of a microscope slide through solvent casting followed by a thermal cure at 110° C. Post cure, the films were submerged in distilled water overnight to extract compounds not bound within the network and release the networks as free-standing, water-swollen films from the substrates.

Topography and Static Contact Angle

Figure 3:
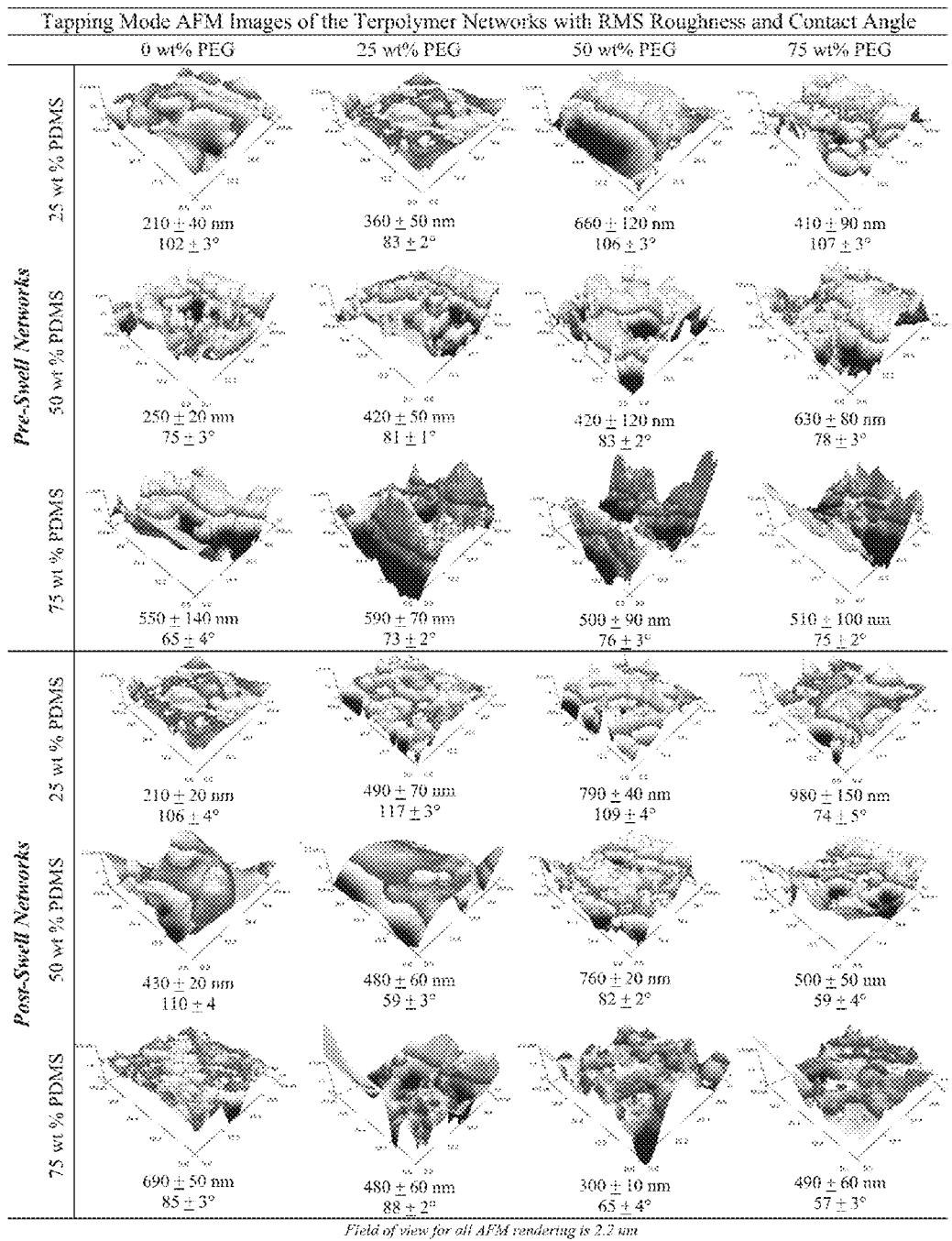
FIG. 3 illustrates tapping mode atomic force microscopy images of terpolymer networks according to weight percent PDMS and PEG relative to the weight of the HBFP.
Figure 4A:
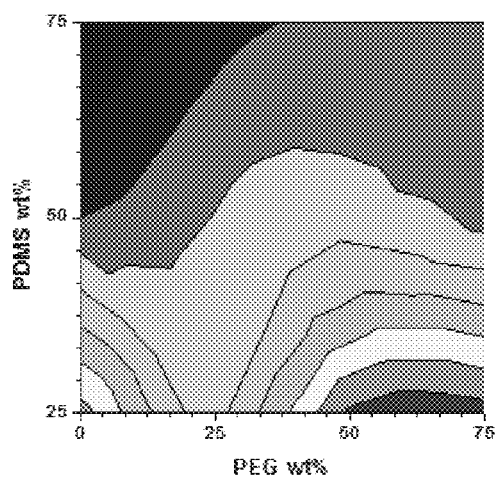
FIGS. 4A and 4B are contour graphs of static water contact angle measurements.
Figure 4B:
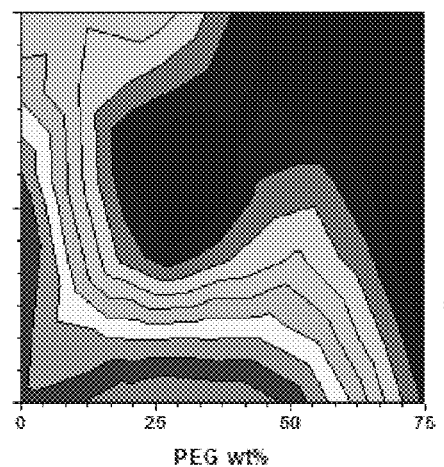
Figure 5:
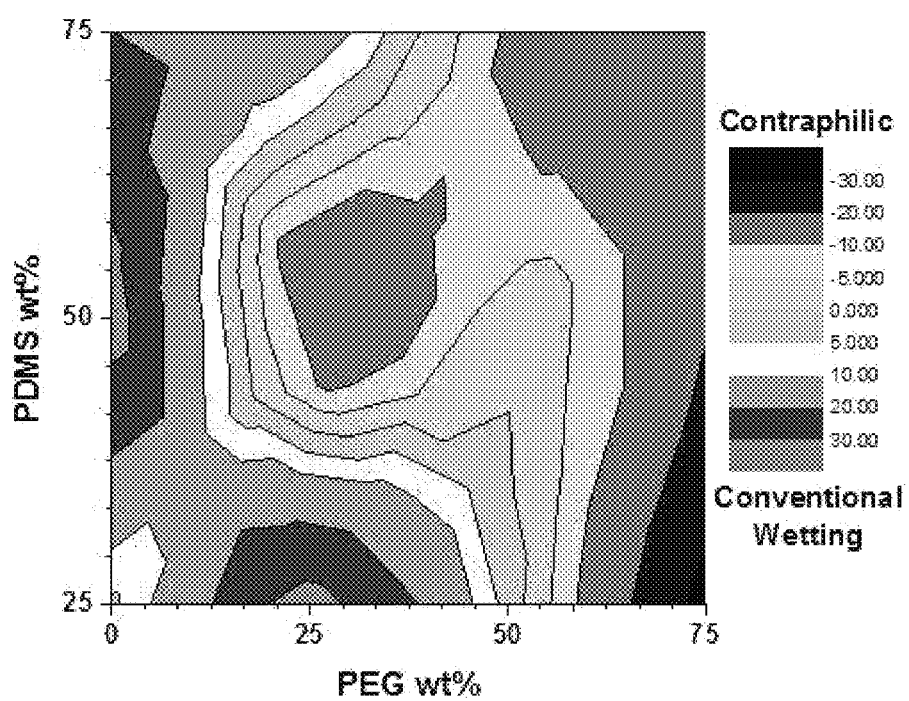
FIG. 5 is a contour graph of the differential static contact angle between dry and water-saturated terpolymer films.
Figure 6A:
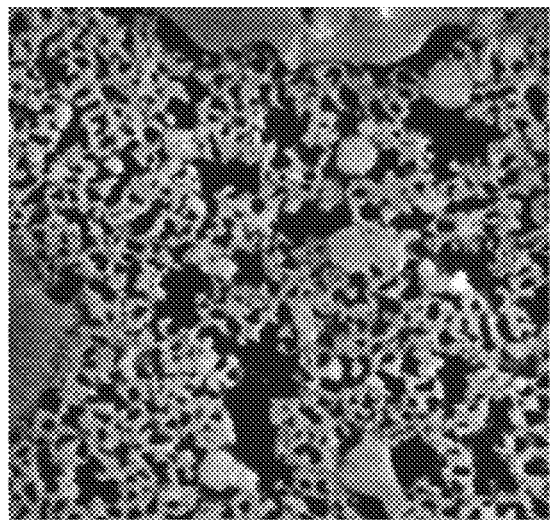
FIGS. 6A-6E are topography and surface force spectroscopy micrographs of a HBFP-PEG-PDMS terpolymer network.
Figure 6B:
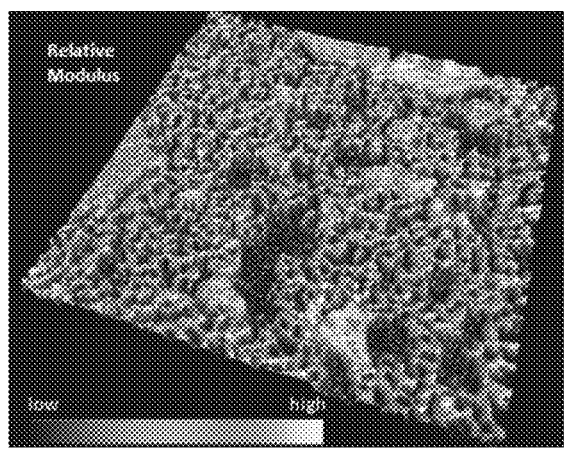
Figure 6C:
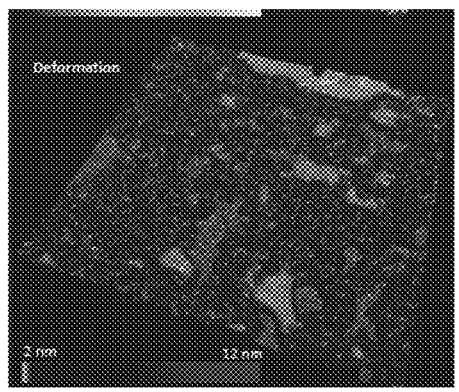
Figure 6D:
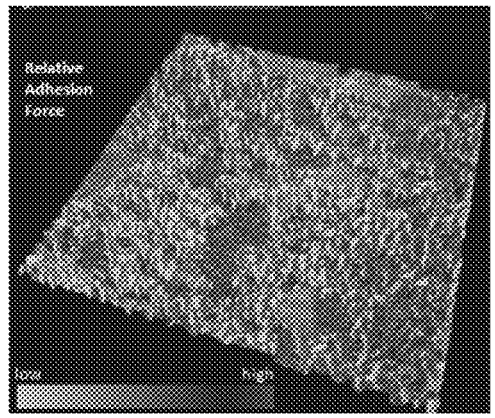
Figure 6E:
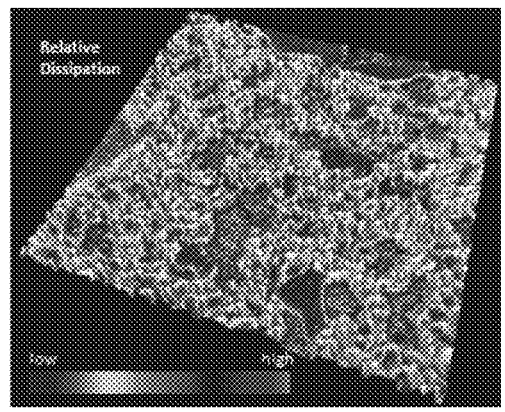

An initial study probed the terpolymer networks with variation of the HBFP-PEG-PDMS weight percent (wt %) ratios to determine the influence of each component on surface character, as evaluated by AFM and contact angle measurements prior to and post water immersion as shown in FIG. 3. In both the dry and wet AFM images, complex topography is seen on the submicrometer scale and surface rearrangement is seen upon water immersion. The dynamic reorganization of the surface chemistry during the water immersion was also probed through static water contact angle measurements. The contact angle data of the dry films (FIG. 4A) show an overall decrease in the hydrophobicity of the surface with increasing amounts of PDMS, displaying that the HBFP fraction plays an integral role in the surface complexity of the system. Upon water immersion (FIG. 4B), a decrease in the contact angle is seen in films with 50 wt % PEG or greater, indicating dynamic surface reorganization occurring in these systems and that the PEG-rich regions are discrete enough for isolated regions of water uptake to occur (FIG. 5). Upon wetting the surfaces having 0 or 25 wt % PEG, an opposite effect was observed, with increases in the static water contact angles (FIG. 5). This behavior has been observed for some amphiphilic materials that are capable of dynamic surface reorganization, where PEG-rich hydrophilic regions absorb water and promote an increase in the fluorocarbon hydrophobic content at the surface, ultimately, resulting in a contraphilic effect, as supported by previous work using secondary ion mass spectrometry (SIMS), and observed in other systems as well.

Surface Compositional Heterogeneity

We next focused attention on the one sample composition that gave the most peculiar behavior. Given the generally high surface topographic roughnesses and trends of either increased or decreased water contact angle, for a minority (0 or 25 wt %) vs. majority (50 or 75 wt %) of PEG content relative to HBFP, respectively, the one sample that was unique was that having 50 wt % of each PEG and PDMS, relative to HBFP, which exhibited no change in water contact angle. In order to determine the contribution of the three constituencies to the surface character of the network, surface force spectroscopy (SFS) mapping was performed to differentiate between HBFP-, PDMS- and PEG-rich regions on the surface of the HBFP-PEG-PDMS terpolymer network with 50 wt % PEG and 50 wt % PDMS ("TP"). A particular focus was placed on the qualitative differences in surface response as a function of topography. The results of the SFS study are provided as AFM micrographs, spectral maps and 3D renderings in FIGS. 6A-6E. Surface topography reveals two sets of features, a raised "lattice" of interconnected features and a lower region interstitial to the "lattice" with a 6.0 nm height differential between the two. However, topography alone tells little in regards to the innate composition of the two regions and would, in a less complex system, imply a biphasic material. To further our understanding of the system's surface, SFS was used to determine the relative difference in surface character from feature to feature. Modulus mapping shows that the raised "lattice" is composed of two major variations in response, with islands of higher modulus material connected by lower modulus material. The deeper, interstitial material appears the softest. Deformation mapping at constant force provides an inverse relationship to that observed from modulus mapping, with the stiff island regions deforming 2 nm, the raised portions connecting the island regions deforming 4 nm and the soft, lowered interstitial regions deforming 10 nm at a constant tapping force. Adhesion force mapping provides similar phase information as what might be assumed from topography, while also suggesting that the height of the features may be directly related to the surface energy where the raised regions are lower energy and the lower regions are rich in higher surface energy material. Dissipation mapping provides information about the energy loss to non-restorative forces after deformation, and correlates with deformation. From what is known about fluoropolymer, PDMS and PEG surfaces in general, the following assignments are made:

1. HBFP-rich regions: Raised islands with high modulus, low deformation, low surface energy and low dissipation.
2. PDMS-rich regions: Raised "lattice" regions between islands with moderate modulus, moderate deformation, low surface energy and moderate dissipation.
3. PEG-rich regions: Deeper interstitial regions with low modulus, high deformation, high surface energy and high dissipation.

Surface Spectroscopy

To further support the results of the SFS findings, attenuated total reflectance infrared spectroscopy (ATR-IR) and X-ray photoelectron spectroscopy (XPS) were used to investigate the surface composition of "TP." ATR-IR provides IR spectra only for the first 100 nm of the sample network surface, making it a viable method for tracking chemical changes in a polymeric surface. Assessment of the surface of "TP" pre- and post-water exposure was performed. The assessment was also done for a PDMS and PEG film and pure HBFP powder. These results are provided in FIG. 7A and FIG. 7B. It can be seen that both the PEG and HBFP samples express water signals almost exclusively after swelling. These results are reasonable, as both the PEG coating and the raw HBFP possess glycol domains which readily uptake water when other constraints do not exist. The PDMS surface displayed only a very small water signature, which is also reasonable. Considering the effects on the surface chemistry of the terpolymer system after wetting, several changes become immediately apparent. From comparison to the PEG surface, it can be seen that the PEG contribution to the 974 $cm^{-1}$ and 1460 $cm^{-1}$ peak signals are greatly diminished after wetting the terpolymer surface. It can also be observed that the HBFP signals at 1497 $cm^{-1}$ and 1734 $cm^{-1}$ are expressly present in the terpolymer surface after wetting.

Figure 7A:
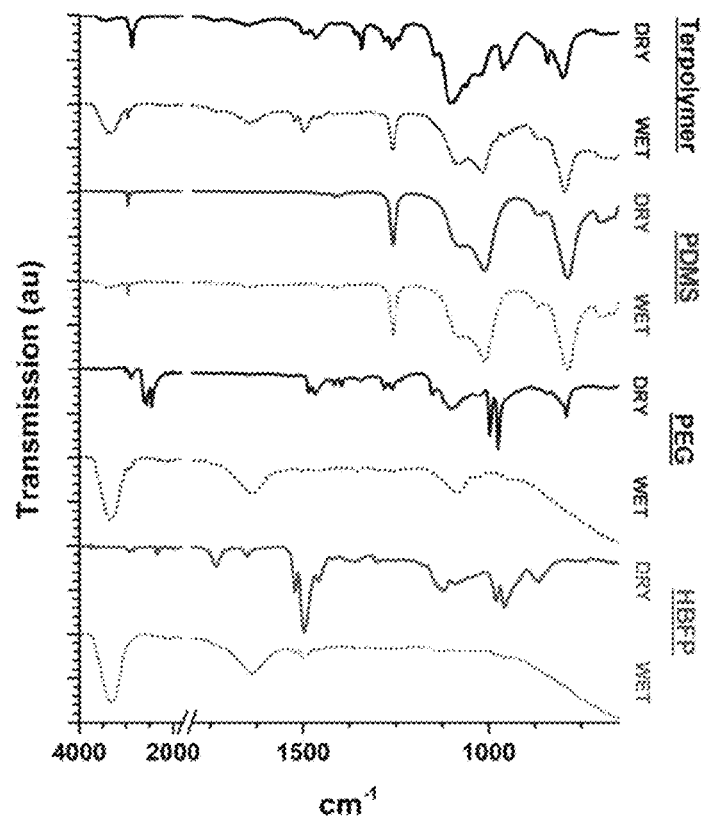
FIG. 7A illustrates attenuated total reflectance infrared spectroscopy spectra for a 2:1:1 HBFP-PEG-PDMS terpolymer network.
Figure 7B:
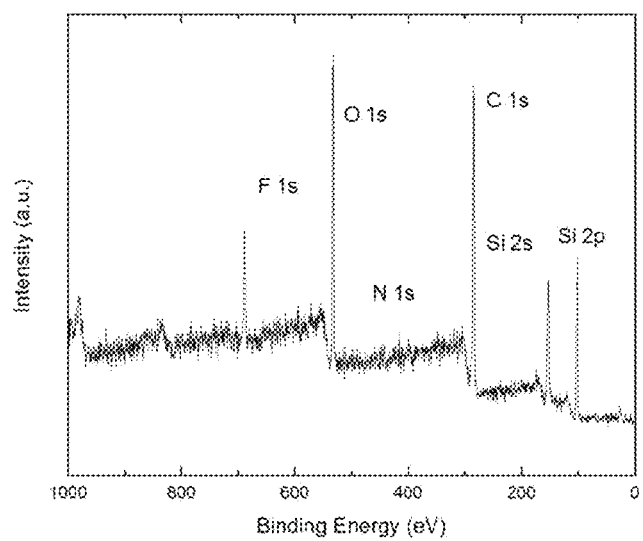
FIG. 7B illustrates X-ray photoelectron spectra for a 2:1:1 HBFP-PEG-PDMS terpolymer network.

Neither of these findings are, in themselves, unique to this system as other HBFP-PEG networks have shown similar behaviors. The uniqueness of this system is in the gross expression of PDMS character after wetting, where the 1010 $cm^{-1}$, 1080 $cm^{-1}$ and 1258 $cm^{-1}$ PDMS peaks dominate the spectra, thus making the overall spectra for the terpolymer surface after wetting most closely mimic the PDMS surface spectral signature. The dominance of the PDMS signature is an important result, as is it implies that HBFP, in the presence of mobile PDMS after water incubation, does not dominate the surface as in other HBFP-PEG systems. This result presents an entirely new method for controlling surface reorganization in these amphiphilic heterogeneous systems, opening a full range of surface controls previously unrealized. XPS results clarify that the surface initially possessed all three functionalities in sufficient quantities to have comparable spectral signatures (FIGS. 7A and 7B).

Thermal Response

Figure 8:
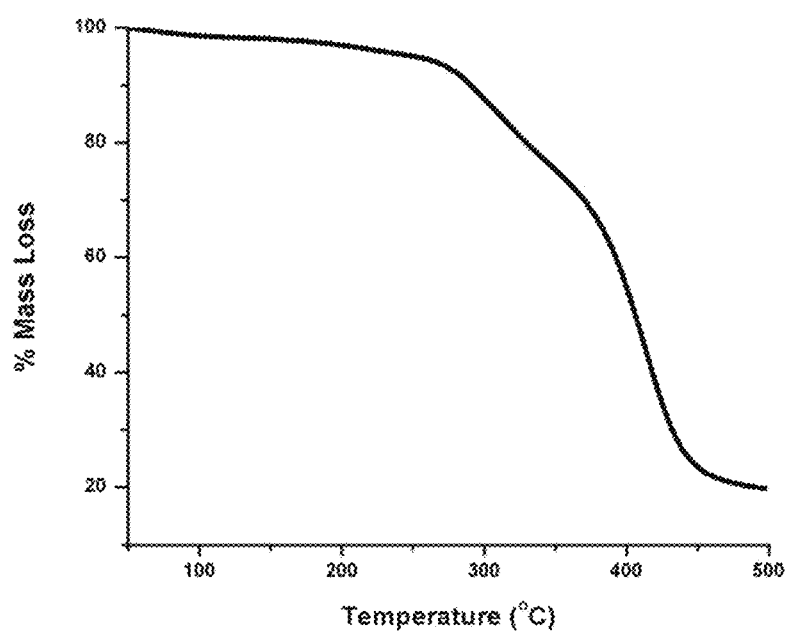
FIG. 8 is a thermogravimetric analysis trace of a HBFP-PEG-PDMS terpolymer network.

TP was investigated by thermogravimetric analysis to determine how crosslinking influences the thermal stability of the network (FIG. 8). From ambient temperature to 250° C., 5% mass loss is seen in the network, consistent with a partial degradation of PDMS. There are then two degradation events that can be seen in the network, the first occurring from 250° C. to ca. 350° C. corresponding to a continued degradation of PDMS, and then from 350° C. to 500° C. resulting in an 80% mass loss of the sample in total, corresponding to the decomposition of HBFP and PEG. It can be seen through this study that the crosslinks in the system do not infer any additional thermal benefit to the network, but overall, this finding should not detract from the intended uses for this material.

Figure 9A:
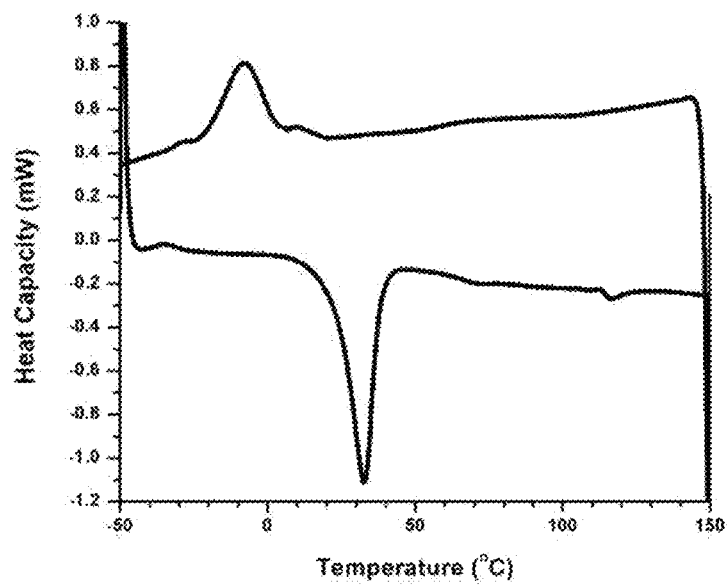
FIG. 9A is a differential scanning calorimetry trace of a HBFP-PEG-PDMS terpolymer network.
Figure 9B:
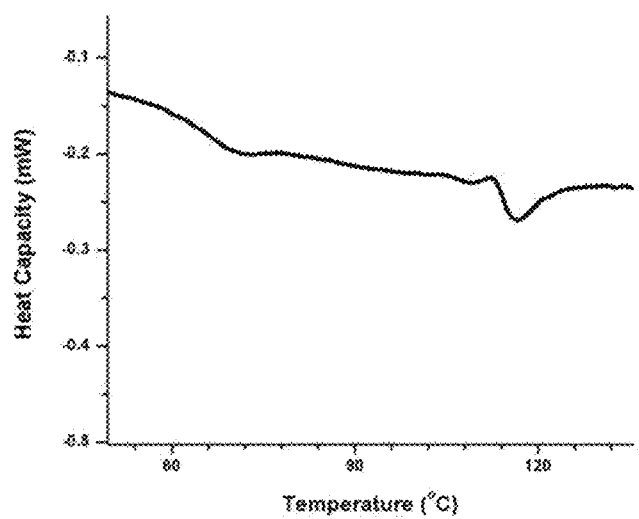
FIG. 9B is an expanded trace of the HBFP-PEG-PDMS terpolymer network.

Differential scanning calorimetry was used to probe the phase transitions present in the terpolymer network (FIGS. 9A and 9B). Upon heating, a melting transition can first be seen at 33° C. which can be attributed to the PEG in the network followed by a $T_g$ at 63° C. which can be attributed to HBFP. A third phase transition, a $T_g$, is then seen at 113° C. which is also attributed to HBFP. HBFP has two unique glass transition temperatures arising from the two units that comprise the framework of the polymer. The $T_g$ at 63° C. is most likely from the branching in the polymer framework in HBFP, with the second $T_g$ arising from linear pentafluorostyrene units.

Mechanical Response

Response in Atmosphere.

Figure 10A:
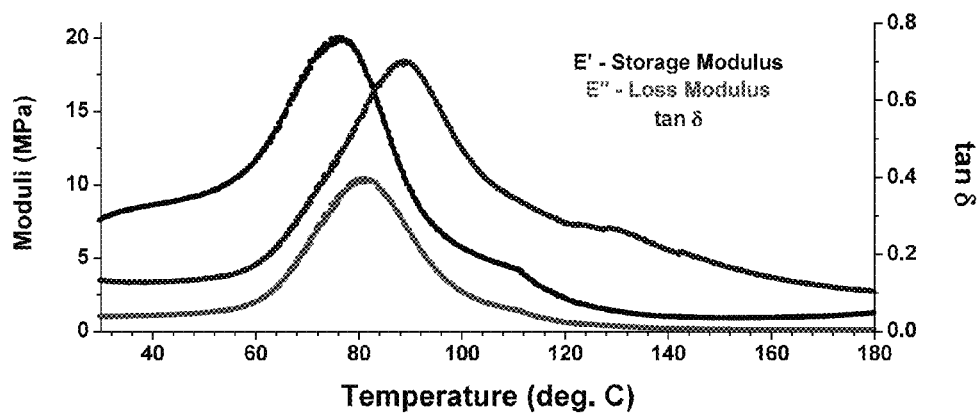
FIG. 10A is a dynamic thermal mechanical analysis graph of a HBFP-PEG-PDMS terpolymer network.
Figure 10B:
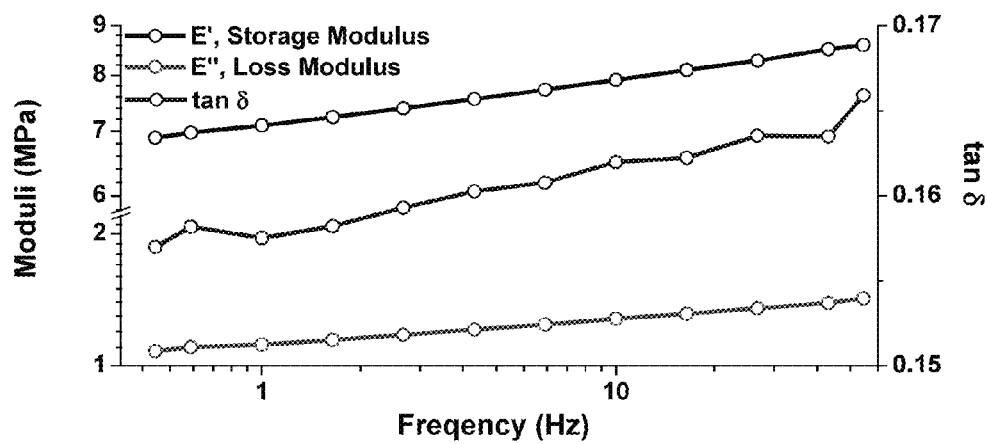
FIG. 10B is a dynamic mechanical analysis graph of the HBFP-PEG-PDMS terpolymer network.

The mechanical properties of TP were investigated with a combination of dynamic mechanical analysis (DMA), dynamic thermal mechanical analysis (DTMA) and static stress-strain analysis. Initial investigation of TP by DTMA at 1 Hz (FIG. 10) showed two phase transitions via tan δ peaks at 89 (A1) and 129° C. (A2), which were assigned to a glass transition of the PEGylated fluorostyrene branching subunits and of the pentafluorosytrene subunits of the HBFP respectively. Room temperature (A0) storage modulus (E') was found to be 7.1 MPa with a loss modulus (E") of 1.1 MPa. A quasi-steady state character was reached near 150° C. (A3), resulting in post-phase transition values of 0.92 and 0.16 MPa for E' and E". A frequency sweep at room temperature displayed frequency dependence typical of an amorphous material without significant phase separations or low temperature phase transitions imminent. A summary of DMA and DTMA data can be found in Table 1. Static stress-strain measurements resulted in a characteristic Young's modulus of 37±1 MPa for deformations of less than 1%.

Response in a Marine Environment.

Figure 11A:
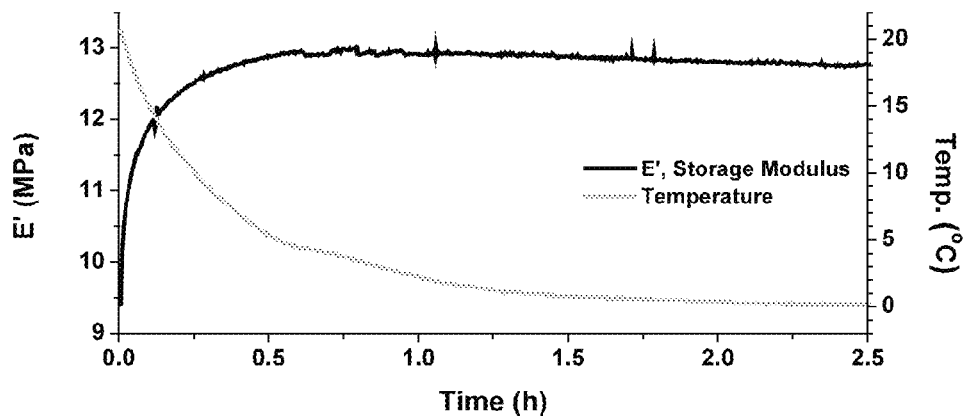
FIGS. 11A-C are dynamic thermal mechanical analysis graph of a HBFP-PEG-PDMS terpolymer network.
Figure 11B:
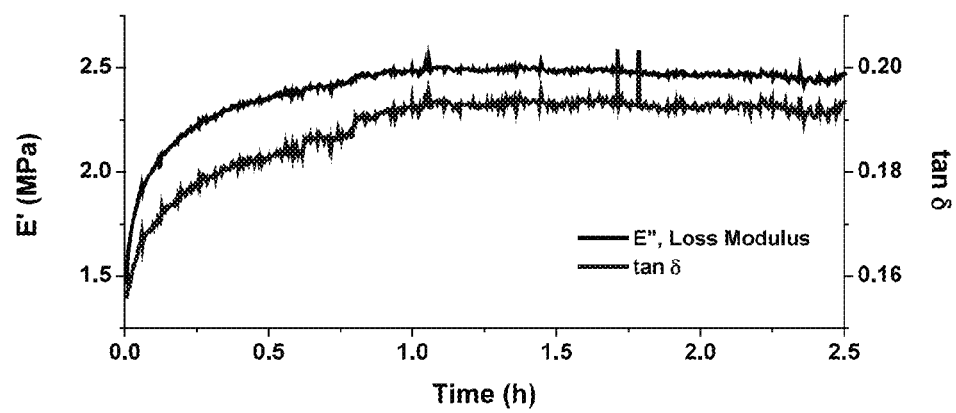
Figure 11C:
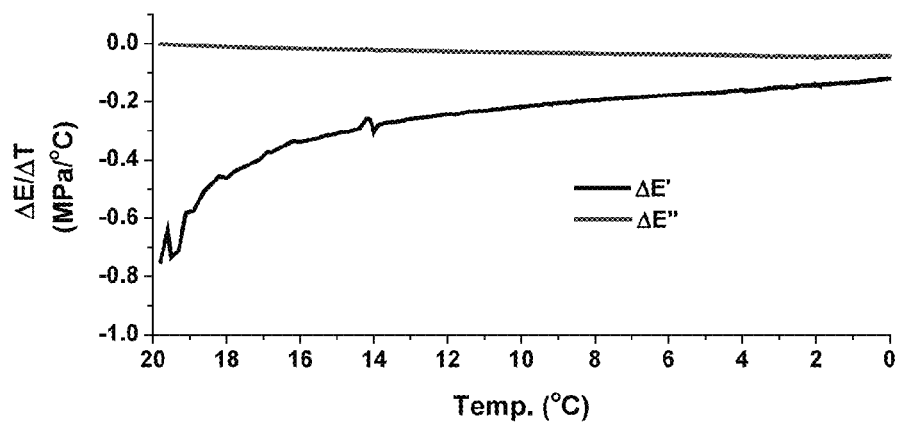

In order to assess the response in a marine setting, one of the target application environments for these materials, TP was assessed by DTMA in synthetic sea water. Temperature was decreased from 20 (M0) to 0° C. over a two and a half hour period and allowed to equilibrate (M2). The mechanical response of the system over this period is summarized in Table 1, below, including the E'/E"/tan δ inflection point (M1) observed at 10° C. and the equilibration time constant after reaching 0° C. Results of this portion of the mechanical assessment are presented in FIG. 11 with a plot of the change in E'/E" per degree change in temperature, as a function of temperature, to display that at temperatures below 15° C. the effect of temperature on stiffness drops off linearly. The ultimate character of TP at 0° C. was a 25% increase in stiffness over initial submersion response and was 50% more resistant to deformation when compared to the ambient condition response in air.

Response at in-Body Conditions.

Figure 12:
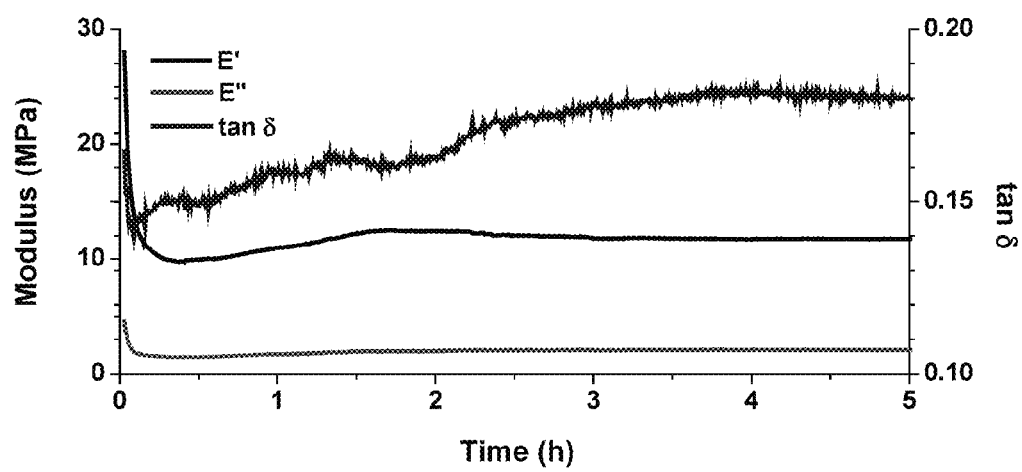
FIG. 12 is submersion dynamic mechanical analysis plot of a HBFP-PEG-PDMS terpolymer network at 37° C. in PBS.

This system also has potential application as a coating on biomedical devices where a decreased likelihood of vector transferal or human cell adhesion is sought. Therefore assessment of the mechanical response of the TP was performed at conditions that simulate an in-body environment. DMA was performed in a submersion of PBS at 37° C. (B0) and monitored to observe solvent uptake (B1 & B2), swelling (B3) and the steady state (B4) response of the film after reaching solvent equilibrium (FIG. 12). Two (relatively) fast phases of initial solvent uptake are observed with transition lifetimes of 0.03 and 0.12 h, and are assigned to rapid association of PEG domains and amphiphilic HBFP domains respectively. These processes resulted in a total loss of ca. 65% of film stiffness. After initial solvent intercalation into the matrix, a swell period of 1.3 h with a transformation lifetime of 0.32 h occurred before beginning an equilibration process resulting in storage and loss moduli similar to that observed in the steady state of the marine application experiment. The similarities are likely a coincidence, as the reasons for both having steady state submersed mechanical properties roughly twice as stiff as the ambient matrix are completely different (e.g. the warmer sample has many rotating bonds in the backbone resulting in a pre-glass transition tensing of the matrix which will dictate mechanical response, whereas rigidity is responsible for the character of the colder sample). However, it is an interesting observation as that TP can be expected to perform similarly in both environments in its current formulation.

Non-Specific Protein Resistance

In an attempt to assess the terpolymer network's surface resistance to non-specific protein binding, an assay was performed using bovine serum albumin (BSA) coupled to Alexa Flour-680. Both TP and a PDMS standard (Sylgard 184) were assessed after 45 min of incubation with a 0.1 mg/mL BSA in PBS buffer via confocal fluorescence microscopy. Comparison of the two surfaces emission histograms from 650 nm to 750 nm after 635 nm excitation can be found in FIG. 13A along with the integrated z-stack images (FIGS. 13B and 13C). The change in relative intensities, with identical excitation and collection regimes, shows TP's surface to be ca. 60% less susceptible to BSA adsorption than the standard Sylgard 184 PDMS surface.

Conclusion

A series of amphiphilic coatings utilizing HBFP, PEG and PDMS with unique surface characteristics were synthesized and characterized. It was shown that heterocomplexity and surface energy are explicitly functions of chemical composition, and that these systems show promise for use as antibiofouling coatings.

TABLE 1

Summary of DMA/DTMA with Kinetics

| | Temp. (deg. C.) | solvent | E' (MPa) | E" (MPa) | tan δ | time (h) | τ (h) | notes |
|---|---|---|---|---|---|---|---|---|
| A0 | 25 | atmosphere | 7.1 | 1.1 | 0.158 | 0 | — | initial |
| A1 | 89 | atmosphere | 10.6 | 7.5 | 0.703 | 1.1 | — | tan δ peak |
| A2 | 129 | atmosphere | 1.5 | 0.39 | 0.270 | 1.8 | — | tan δ peak |
| A3 | 150 | atmosphere | 0.92 | 0.16 | 0.173 | 2.1 | — | high T ss |
| M0 | 20 | sea water | 10.4 | 1.6 | 0.159 | 0 | — | initial |
| M1 | 10 | sea water | 12.5 | 2.2 | 0.178 | 0.3 | — | — |
| M2 | 0 | sea water | 12.8 | 2.5 | 0.193 | 2 | 0.07 ± 0.01 | ss |
| B0 | 37 | PBS | 28.0 | 4.6 | 0.164 | 0 | — | initial |
| B1 | 37 | PBS | 13.1 | 1.9 | 0.104 | 0.1 | 0.03 ± 0.01 | solvation 1 |
| B2 | 37 | PBS | 9.8 | 1.5 | 0.151 | 0.4 | 0.12 ± 0.01 | solvation 2 |
| B3 | 37 | PBS | 12.5 | 2.0 | 0.161 | 1.7 | 0.32 ± 0.04 | swell |
| B4 | 37 | PBS | 11.7 | 2.1 | 0.180 | 5 | 0.61 ± 0.09 | ss |

Differing from previous fluoropolymer-PEG systems through incorporation of PDMS, the synthesized terpolymer system expands on the current generation of coatings and displays distinctive topographical, compositional and morphological features, as seen specifically through the analysis of the surfaces by surface force and ATR-IR spectroscopies. The systems presented here provide enhanced surface complexity with no significant increase in the synthetic or cure conditions. This system also provides an entirely new mode of dynamic surface reorganization as shown by preferential emergence of PDMS character on the surface after water immersion and differing from the heavy fluoropolymer expression observed in previous HBFP-PEG formulations.

By varying the compositional ratios of the three constituents, a wide range of topographical, hydroscopic and swell-reorganization variations were displayed. Microscopic characterization revealed a highly disordered heterogeneous surface that varied both topographically and chemically at the micro- and nano-scale. Investigation of non-specific protein binding resistance of the terpolymer network is encouraging; with significantly better resistance to protein adsorption than a commercially available anti-biofouling PDMS standard.

Bulk thermal and mechanical characterization revealed the kinetics and degree of matrix change at both marine and in-body conditions. All of these features provide a new type of amphiphilic surface uniquely qualified for further investigation as a new branch of anti-biofouling material.

Example 2

Mitigation of Biofouling

Anti-biofouling surfaces were produced by synthesis of terpolymer coatings composed of hyperbranched fluoropolymers crosslinked with bisamino-propyl poly(ethylene glycol) and bisamino-propyl polydimethylsiloxane (PDMS). This HBFP was chosen, due to its amphiphilic character, which enhances anti-biofouling performance while retaining the desired nanoscale surface heterogeneities. Crosslinking in this system occurred via a substitution reaction of the bromoacetyl and bromobenzyl groups of HBFP with the amine termini of both the linear PEG and PDMS crosslinkers. Nanoscale imaging and surface spectroscopy confirmed that this system possessed complex surface topographies and chemical compositions. Surface complexity was determined to be due to molecular interactions, phase segregation and compositional gradients arising between the three components. A clear difference in surface behaviour was observable before and after exposure to water. Anti-biofouling characteristics were investigated by bovine serum albumin (BSA) adhesion studies, displaying a 60% greater resistance to protein adsorption, in comparison to the fouling of a PDMS standard.

An array of HBFP-PEG-PDMS were produced to investigate the anti-biofouling performance of the coatings. The amounts of the crosslinkers were varied with respect to HBFP to create a 3×3 array of coatings with varying weight percentages of PEG and PDMS (25 wt %, 50 wt % and 75 wt %) to determine which composition and properties afford the most promising characteristics for future anti-biofouling coatings.

A range of test coatings were prepared for evaluation. Coatings were mounted on an epoxy barrier coat (Interseal 670HS). Generally, the two component system of Interseal 670HS was mixed per the manufacturer's instructions (5.70 mL:1 mL of Part A:Part B) and was then diluted with 3 mL of THF. The system was applied to a glass microscope slides via an airbrush applicator (Central Pneumatic) using an application pressure of 50 psi. The system allowed to cure at ambient temperature for 18 hours. To a scintillation vial was added a selected HBFP (370 mg, 0.032 mmol)), 1500 Da bis(3-aminopropyl)-terminated PEG (92.5 mg, 0.062 mmol, 25 wt %), 1500 Da bis(3-aminopropyl)-terminated PDMS (92.5 mg, 0.037 mmol, 25 wt %), THF (20 mL) and N,N-diisopropylethylamine (DIPEA) (0.050 mL, 0.30 mmol) and the mixture was svortexed until homogeneous. The film was then applied to 8 coated glass microscope slides via an airbrush applicator using an application pressure of 50 psi. The film was then cured in an oven at 110° C. for 45 min under N2 atmosphere to afford the dry coatings. Slides coated with only the barrier coat (under-coat) were supplied as a control to check that it was not affecting the attachment of the diatoms. Water contact angles for the coatings were evaluated to estimate hydrophobicity.

TABLE 1

List of test coatings showing weight percentages of PEG and PDMS in the HBFP terpolymer coatings and associated water contact angles

| No. U coat | % PEG Interseal | % PDMS under-coat | Con Ang dry | Con Ang wet |
|---|---|---|---|---|
| 1 | 25 | 25 | 83.7 + 3.7 | 107.4 + 2.8 |
| 2 | 25 | 50 | 80.7 + 2.5 | 89.4 + 2.6 |
| 3 | 25 | 75 | 76.8 + 3.6 | 83.6 + 3.5 |
| 4 | 50 | 25 | 109.2 + 6.2 | 101.8 + 4.2 |
| 5 | 50 | 50 | 100.9 + 5.5 | 108.9 + 4.0 |
| 6 | 50 | 75 | 73.5 + 4.4 | 84.9 + 2.2 |
| 7 | 75 | 25 | 97.7 + 3.1 | 107.9 + 4.0 |
| 8 | 75 | 50 | 85.2 + 5.1 | 103.5 + 1.3 |
| 9 | 75 | 75 | 86.6 + 4.9 | 79.3 + 2.8 |

Methods

Generally, standard methods were used.

Coating Equilibration in Seawater

All coatings were equilibrated in de-ionised water for 24 hours followed by 0.22 μm filtered artificial seawater for 2 hours prior to testing.

Initial Attachment (Density of Cells Attached after Gentle Washing)

Figure 14:
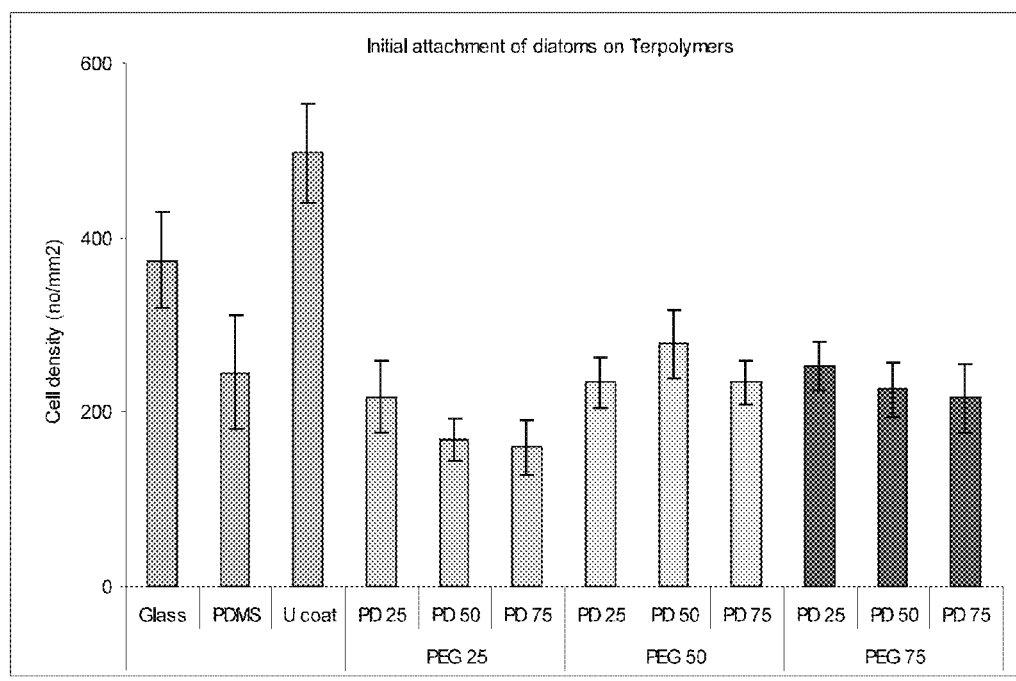
FIG. 14 is a graph of initial attachment of diatoms on HBFP-PEG-PDMS terpolymer coatings having various compositions.

N incerta cells were cultured in F/2 medium contained in 250 ml conical flasks. After 3 days the cells were in log phase growth. Cells were washed 3 times in fresh medium before harvesting and diluted to give a suspension with a chlorophyll a content of approximately 0.25 μg ml−1. Cells were settled in individual dishes containing 10 ml of suspension at room temperature on the laboratory bench. After 2 hours the slides were exposed to a submerged wash in seawater to remove cells which had not attached (the immersion process avoided passing the samples through the air-water interface). Samples were fixed in 2.5% glutaraldehyde, air dried and the density of cells attached to the surface was counted on each slide using a fluorescence microscope. Strong autofluorescence from the samples meant that counting could not be automated and counts were made by eye. Counts were made for 10 fields of view (each 0.15 mm2) on each slide. Results are shown in FIG. 14.

Strength of Attachment

Figure 15:
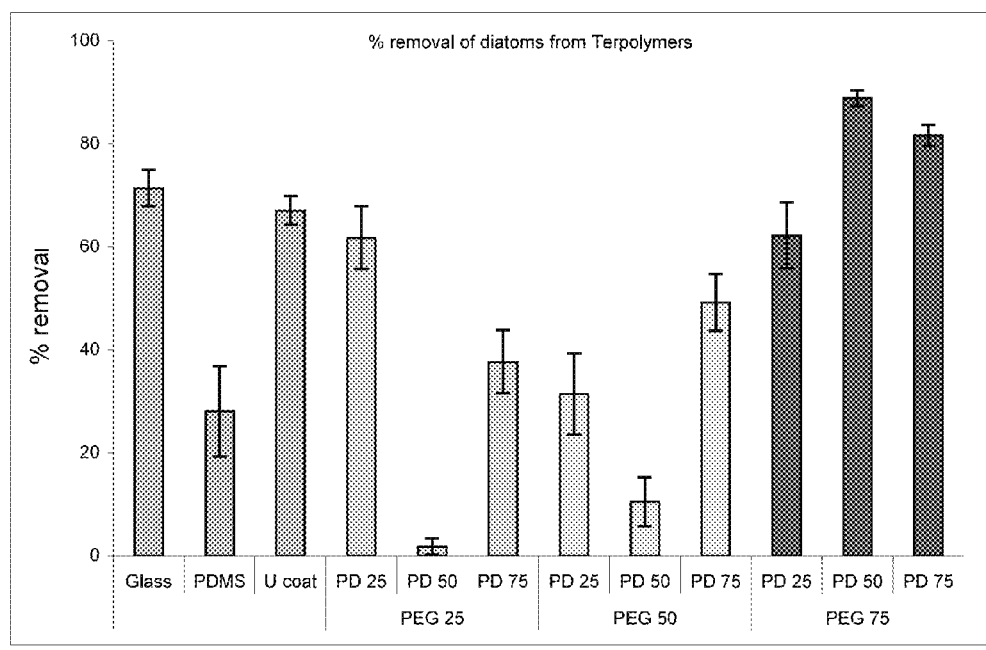
FIG. 15 is a graph of water channel removal of diatoms on HBFP-PEG-PDMS terpolymer coatings having various compositions.
Figure 16:
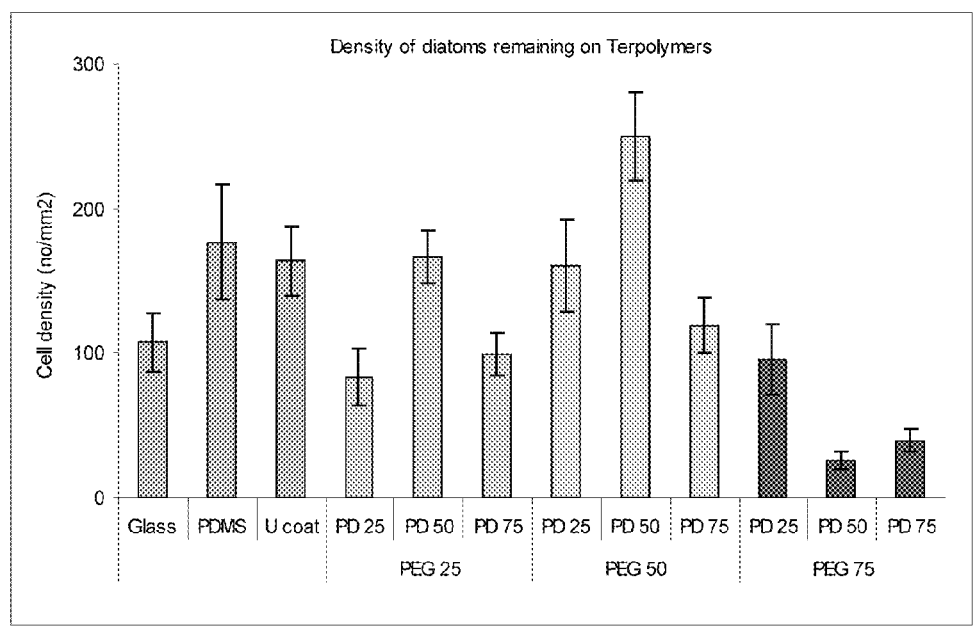
FIG. 16 is a graph of density of diatoms remaining after water channel removal from HBFP-PEG-PDMS terpolymer coatings having various compositions.

Slides with attached cells of N. incerta were exposed to a shear stress of 20 Pa in a water channel. Samples were fixed and the number of cells remaining attached was counted using the method described above. Results are shown in FIG. 15. The density of attached N. incerta on the test coatings after washing i.e. initial attachment density is illustrated in FIG. 16. Each point is the mean from 30 counts on 3 replicate slides. Bars show 95% confidence limits.

Settlement of Zoospores

Figure 17:
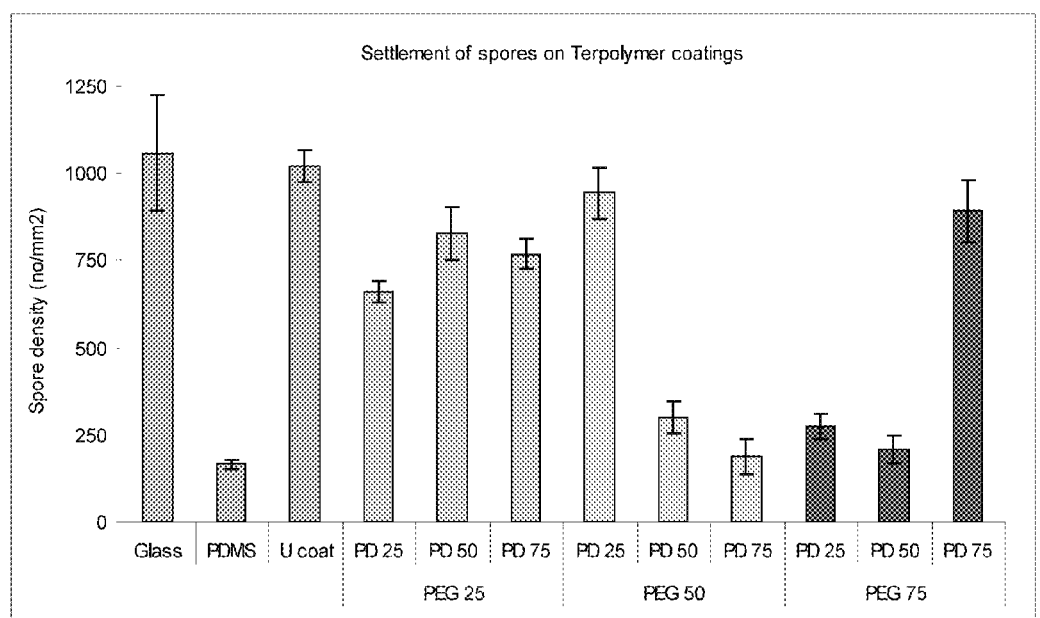
FIG. 17 is a graph of spore settlement on HBFP-PEG-PDMS terpolymer coatings having various compositions.

Zoospores were obtained from mature plants of *U. linza* by the standard method. A suspension of zoospores (10 ml; 1×106 spores ml−1) was added to individual compartments of quadriperm dishes containing the samples. After 45 minutes in darkness at room temperature, the slides were washed by passing 10 times through a beaker of seawater to remove unsettled (i.e. swimming) spores. Slides were fixed using 2.5% glutaraldehyde in seawater. The density of zoospores attached to the surface was counted on each of 3 replicate slides using an image analysis system attached to a fluorescence microscope. Spores were visualised by autofluorescence of chlorophyll. Counts were made for 30 fields of view (each 0.15 mm$^2$) on each slide. Results are shown in FIG. 17.

Growth of Sporelings

Spores were allowed to settle on the coatings for 45 minutes and then washed as described above. The spores were cultured using supplemented seawater medium for 7 days to produce sporelings (young plants) on 6 replicate slides of each treatment. Sporeling growth medium was refreshed every 48 hours.

Figure 18:
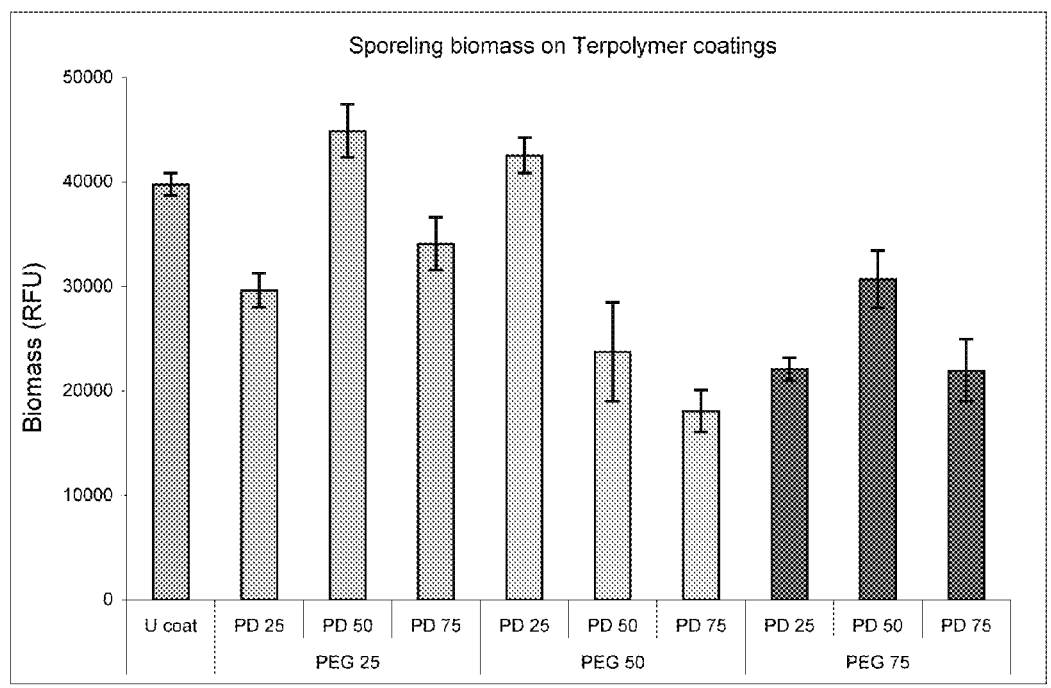
FIG. 18 is a graph of sporeling growth on HBFP-PEG-PDMS terpolymer coatings having various compositions.

Sporeling biomass was determined in situ by measuring the fluorescence of the chlorophyll contained within the sporelings in a Tecan fluorescence plate reader. Using this method the biomass was quantified in terms of relative fluorescence units (RFU). The RFU value for each slide is the mean of 70 point fluorescence readings taken from the central portion. The sporeling growth data are expressed at FIG. 18 as the mean RFU of 6 replicate slides; bars show SEM (standard error of the mean).

Strength of Attachment of Sporelings

Figure 19:
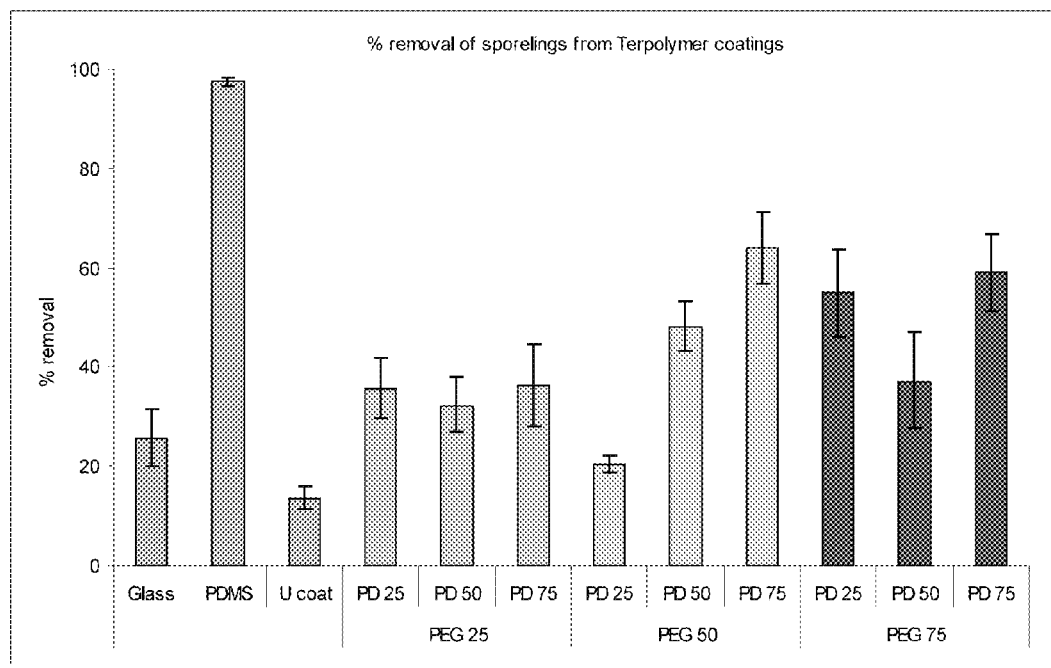
FIG. 19 is a graph of water channel removal of sporelings from HBFP-PEG-PDMS terpolymer coatings having various compositions.

Strength of attachment of sporelings was initially assessed using a shear stress of 52 Pa in the water channel (52 Pa is the maximum achievable). There was negligible removal from any of the terpolymer coatings and consequently the apparatus was changed for the higher powered water jet. The relative attachment strength of sporelings on the terpolymer coatings was determined by exposure to a water jet producing an impact pressure of 112 kPa. Biomass remaining after exposure to the water jet was determined using the fluorescence plate reader (as above). The percentage removal as shown at FIG. 19 was calculated from readings taken before and after exposure to the water jet.

Results & Discussion

Initial Attachment of Diatoms:

Diatoms sink in the water column and land on the coating surfaces by gravity. Therefore, before washing, the cell density on all the test surfaces is the same, irrespective of chemistry. The process of washing removes unattached and weakly attached cells and thus differences in initial attachment density reflect differences in the ability of cells to attach firmly to the surfaces and resist the hydrodynamic forces of washing.

The initial attachment densities of diatoms were broadly similar on all the terpolymer test coatings (FIG. 14). Attachment densities were higher on the glass standard and on the Interseal undercoat.

Strength of Attachment of Diatoms

Diatom removal due to a shear stress of 20 Pa was higher from the three coatings containing PEG at 75 wgt % than from the other coatings (FIG. 15). Removal was exceptionally low from the coatings containing PEG at 25 and 50 wgt % in conjunction with PDMS at 50 wgt %.

The density of diatoms remaining on the terpolymer coatings was lowest on the coatings containing PEG at 75 wgt % in conjunction with PDMS at 50 and 75 wgt % (FIG. 16).

Settlement of Zoospores

Spore settlement density on the terpolymer coatings differed between formulations (FIG. 17). On the PEG 25 coatings, settlement density was similar at all PDMS loadings. However, on the PEG 50 coatings settlement density decreased with PDMS content, whilst on the PEG 75 coatings it increased.

Growth of Sporelings

Figure 20A:
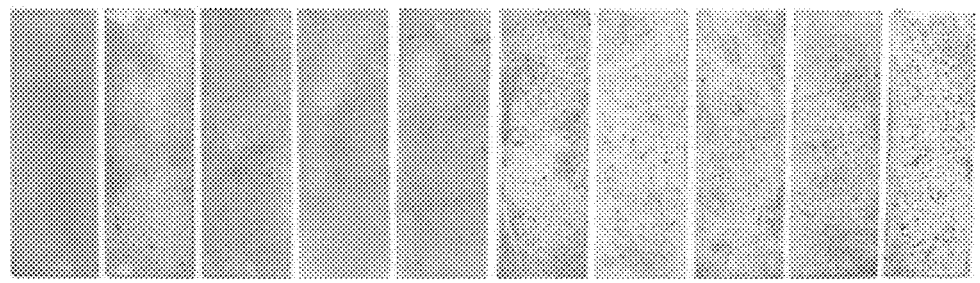
FIG. 20A illustrates growth of sporelings on HBFP-PEG-PDMS terpolymer coatings having various compositions after 7 days.
Figure 20B:
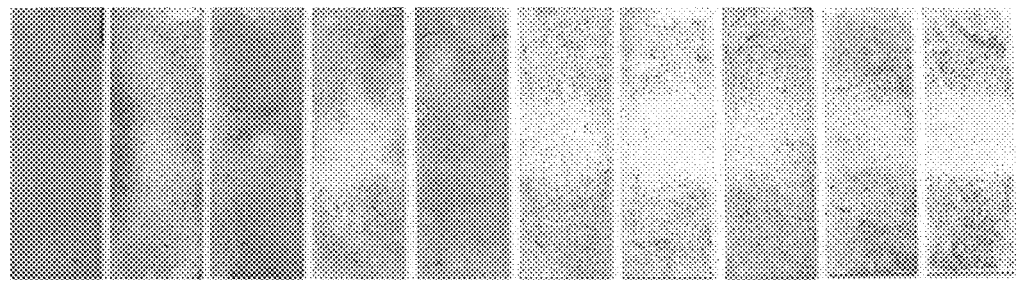
FIG. 20B illustrates sporelings remaining after exposure to shear stress of 160 kPa.

Biomass generation on all coatings broadly reflected the spore settlement densities described above (FIG. 18). Sporeling growth appeared normal on all coatings with no signs of toxicity (FIGS. 20A and 20B) (from left, the coatings illustrated in FIGS. 20A and 20B are: Control; PEG 25+PD 25, 50, 75; PEG 50+PD 25, 50, 75; PEG 75+PD 25, 50, 75).

Strength of Attachment of Sporelings

The percent removal of sporelings is shown in FIG. 19. None of the coatings had a fouling-release performance that was as good as the PDMSe standard. Adhesion strength on the PEG 25 coatings was similar at all PDMS loadings. On the PEG 50 coatings adhesion strength decreased with PDMS content i.e. % removal increased as PDMS content increased. On the PEG 75 coatings adhesion strength was slightly higher (i.e. less removal) on the PDMS 50% loading than on the 25 and 75% loadings.

At a PEG content of 25%, neither antifouling (spore settlement) or fouling-release performance were affected by PDMS content. When the PEG content was increased to 50%, spore settlement density and adhesion strength both decreased as the PDMS content increased.

The disclosed subject matter is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of each of which is incorporated herein by reference in its entirety for all purposes.

The invention claimed is:

1. A composition for reducing or mitigating biofouling, the composition comprising a compound represented by Formula A:

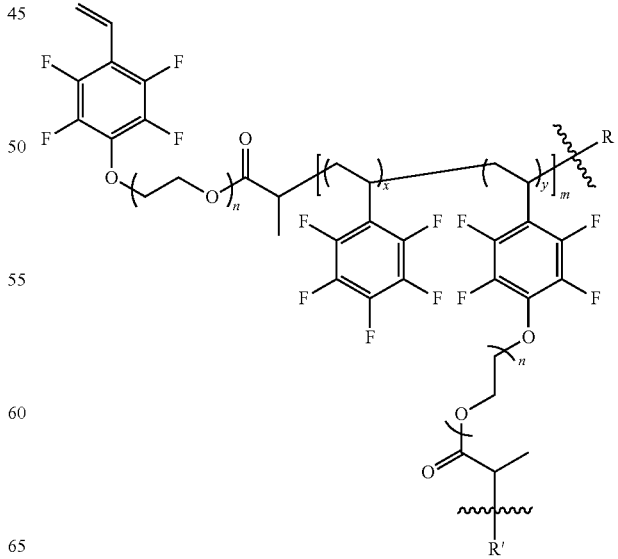

(Formula A)

wherein:
n is selected from an integer between 1 and 15 inclusive;
x is selected from a number between 0.01 and 0.99, where y=(1-x);
m is selected from an integer between 1 and 250 inclusive;
R is selected from the group consisting of

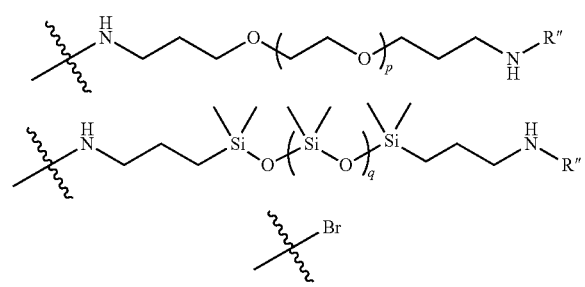

and R' is selected from the group consisting of

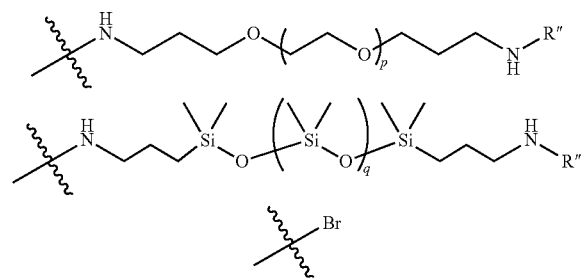

wherein p and q are integers independently selected from between 1 and 250 inclusive and R" is another domain of Formula A or Hydrogen, and
wherein the weight percentage of diamino-polyethylene glycol is between about 0.5% and about 99% of the weight of the compound.

2. A composition for reducing or mitigating biofouling, the composition comprising a compound represented by Formula A:

(Formula A)

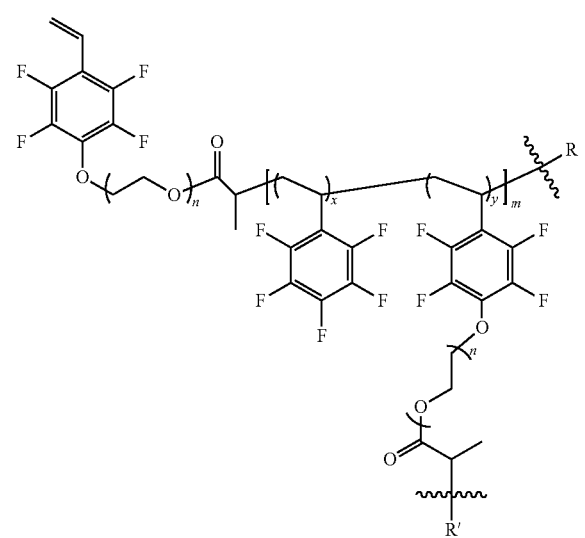

wherein:
n is selected from an integer between 1 and 15 inclusive;
x is selected from a number between 0.01 and 0.99, where y=(1-x);
m is selected from an integer between 1 and 250 inclusive;
R is selected from the group consisting of

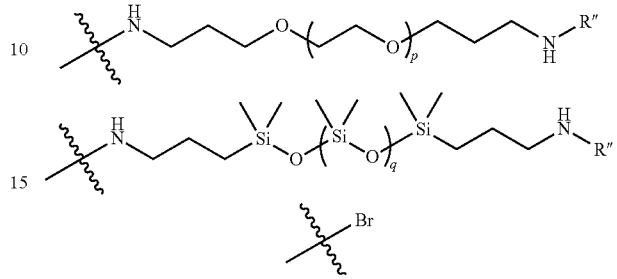

and R' is selected from the group consisting of

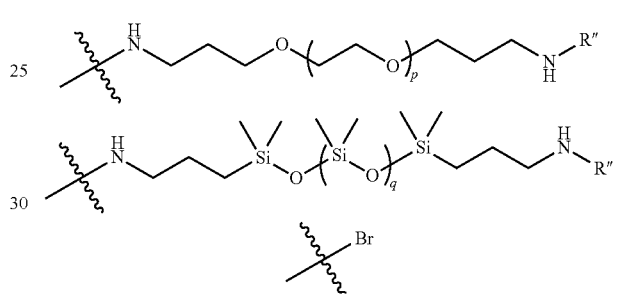

wherein p and q are integers independently selected from between 1 and 250 inclusive and R" is another domain of Formula A or Hydrogen, and
wherein the weight percentage of diamino-polydimethyl-siloxane is between about 0.5% and about 99% of the weight of the compound.

3. A composition for reducing or mitigating biofouling, the composition comprising a compound represented by Formula A:

(Formula A)

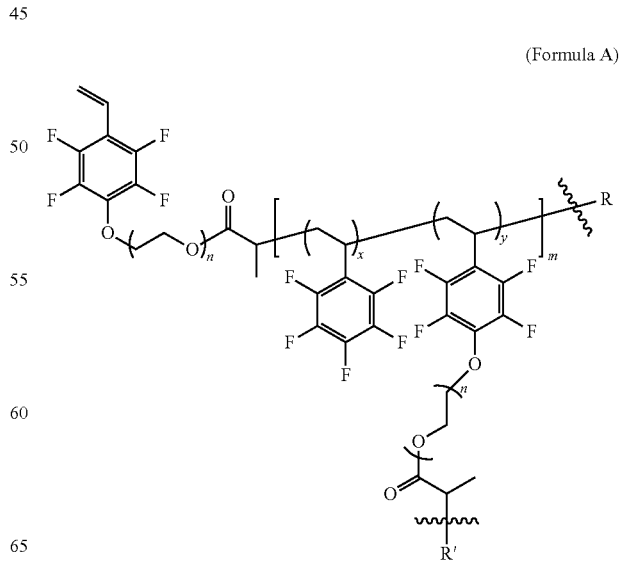

wherein:
n is selected from an integer between 1 and 15 inclusive;
x is selected from a number between 0.01 and 0.99, where y=(1−x);
m is selected from an integer between 1 and 250 inclusive;
R is selected from the group consisting of

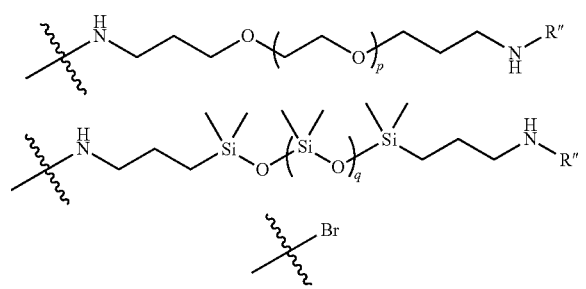

and R' is selected from the group consisting of

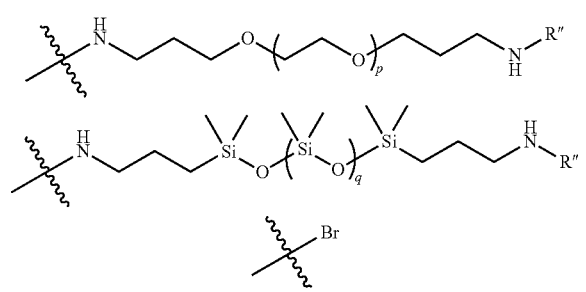

wherein p and q are integers independently selected from between 1 and 250 inclusive and R" is another domain of Formula A or Hydrogen, and wherein the weight percentage of diaminopolyethylene glycol is between about 17.5% and about 30% of the weight of the compound.

4. A composition for reducing or mitigating biofouling, the composition comprising a compound represented by Formula A:

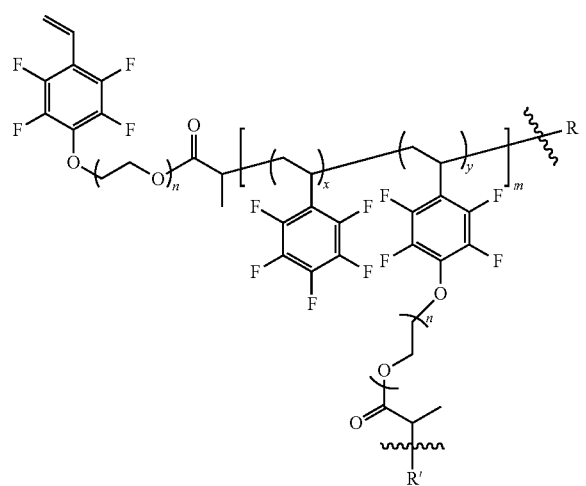

(Formula A)

wherein:
n is selected from an integer between 1 and 15 inclusive;
x is selected from a number between 0.01 and 0.99, where y=(1−x);

m is selected from an integer between 1 and 250 inclusive;
R is selected from the group consisting of

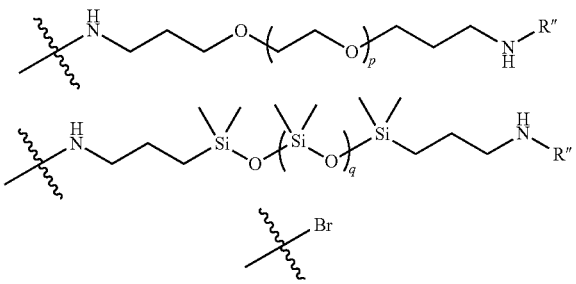

and R' is selected from the group consisting of

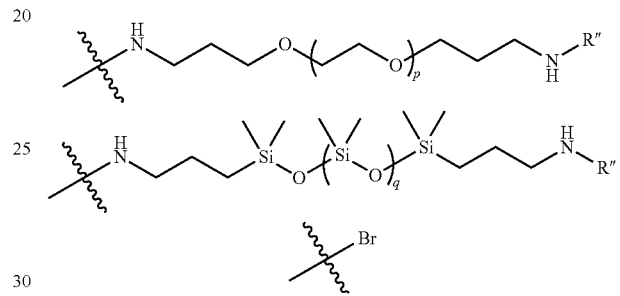

wherein p and q are integers independently selected from between 1 and 250 inclusive and R" is another domain of Formula A or Hydrogen, and wherein the weight percentage of diamino-polydimethyl-siloxane is between about 17.5% and about 30% of the weight of the compound.

5. A composition for reducing or mitigating biofouling, the composition comprising a compound represented by Formula A:

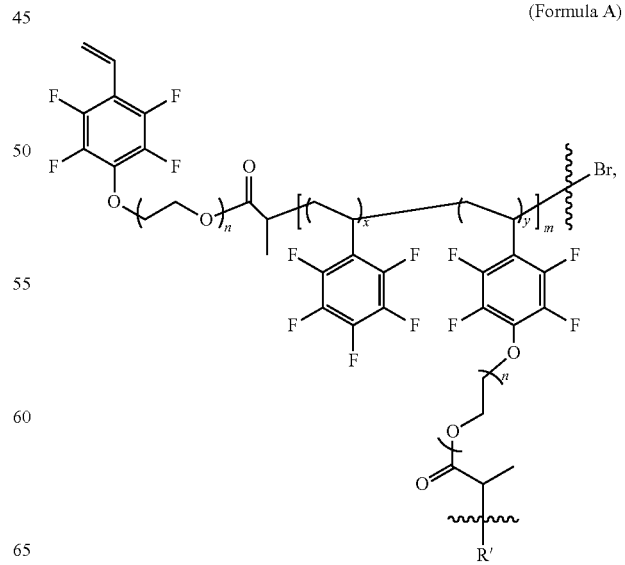

(Formula A)

wherein:
n is selected from an integer between 1 and 15 inclusive;
x is selected from a number between 0.01 and 0.99, where y=(1−x);
m is selected from an integer between 1 and 250 inclusive;
R is selected from the group consisting of

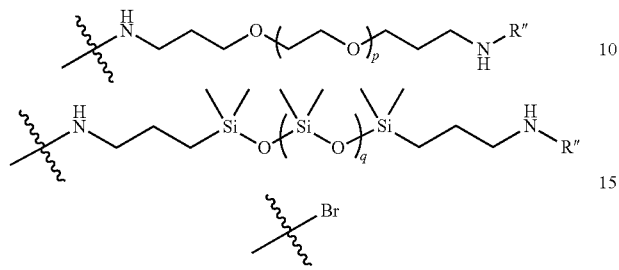

and R' is selected from the group consisting of

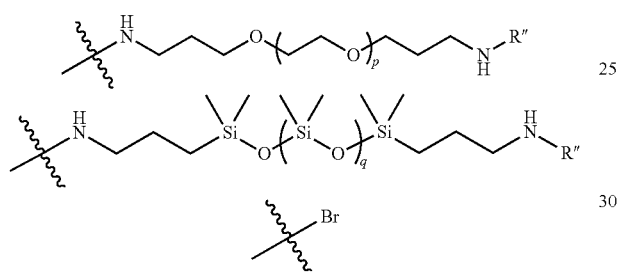

wherein p and q are integers independently selected from between 1 and 250 inclusive and R" is another domain of Formula A or Hydrogen, and
wherein the weight percentage of diaminopolyethylene glycol is between about 17.5% and about 30% of the weight of the compound and the weight percentage of diamino-polydimethylsiloxane is between about 17.5% and about 30% of the weight of the compound.

6. The composition of claim 1, wherein the compound comprises a heterogeneous distribution of chemical domains.

7. The composition of claim 6, wherein the compound comprises a heterogeneous distribution of hydrophobic and hydrophilic domains.

8. The composition of claim 1, wherein the compound exhibits topographical heterogeneity at the microscale and at the nanoscale.

9. The composition of claim 1, wherein the compound comprises a raised region, a lattice region, and a deeper interstitial region.

10. The composition of claim 9, wherein
the raised region is characterized by a high modulus, a low deformation, a low surface energy, and low dissipation;
the lattice region is characterized by a moderate modulus, a moderate deformation, a low surface energy, and a moderate dissipation; and
the deeper interstitial region is characterized by a low modulus, a high deformation, a high surface energy, and a high dissipation.

11. A method for preparing a compound for reducing or mitigating biofouling comprising:
(a) reacting 2,3,4,5,6-pentafluorostyrene with polyethylene glycol to obtain a product represented by Formula I below:

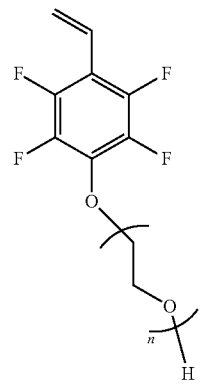

(I)

wherein n is selected from an integer between 1 and 15 inclusive;
(b) reacting the product obtained in (a) with 2-bromopropionyl bromide to obtain a product represented by Formula II below:

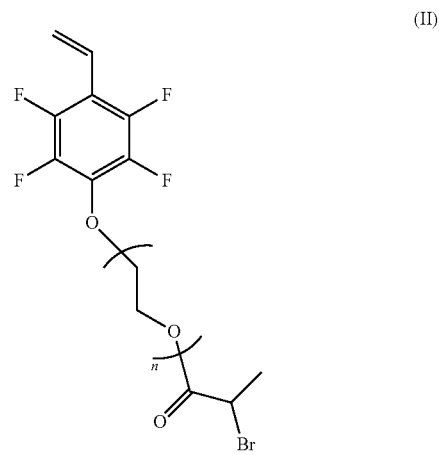

(II)

and (c) reacting the product obtained in (b) with 2,3,4,5,6-pentafluorostyrene to obtain a branched fluoropolymer represented by Formula III below:

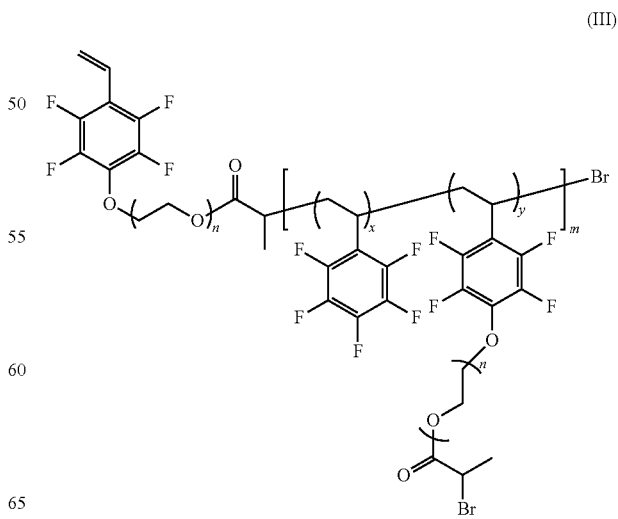

(III)

wherein n is selected from an integer between 1 and 15 inclusive; x is selected from a number between 0.01 and 0.99, where y=(1−x); and m, q, and p are independently selected from an integer between 1 and 250 inclusive; and (d) reacting the branched fluoropolymer obtained in (c) with bisaminopropyl-polyethylene glycol having between 1 and 250 monomer units and bisaminopropyl-polydimethylsiloxane having between 1 and 250 monomer units to obtain a terpolymer of the branched fluoropolymer, polyethylene glycol and polydimethylsiloxane, wherein the weight percentage of diamino-polyethylene glycol is between about 0.5% and about 99% of the weight of the compound.

12. The method of claim 11, wherein the terpolymer of the branched fluoropolymer, polyethylene glycol and polydimethylsiloxane obtained is represented by the compound of Formula A below

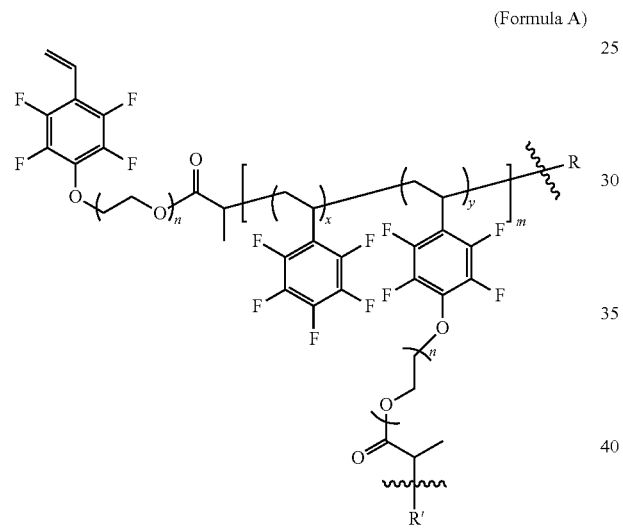

(Formula A)

wherein R is selected from the group consisting of

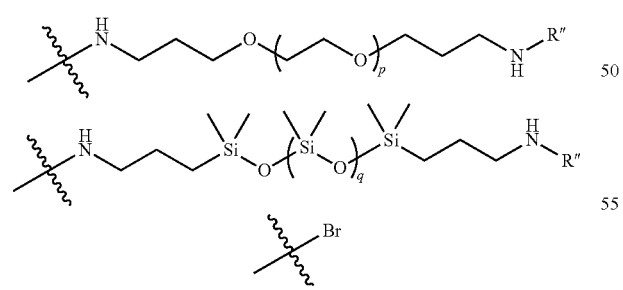

and R' is selected from the group consisting of

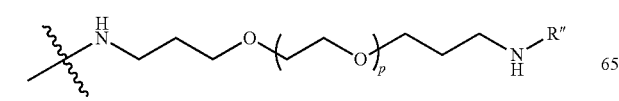

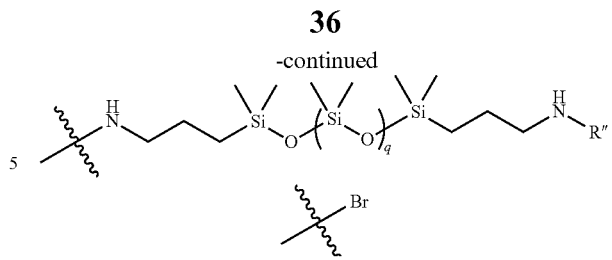

wherein R″ is another domain of Formula A or Hydrogen.

13. The method of claim 11, wherein the terpolymer of the branched fluoropolymer, polyethylene glycol and polydimethylsiloxane is represented by Compound Q.

14. A method for preparing a compound for reducing or mitigating biofouling comprising:

(a) reacting 2,3,4,5,6-pentafluorostyrene with polyethylene glycol to obtain a product represented by Formula I below:

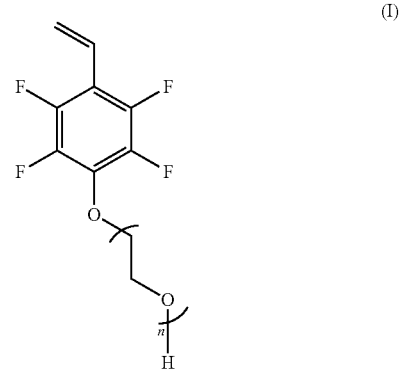

(I)

wherein n is selected from an integer between 1 and 15 inclusive;

(b) reacting the product obtained in (a) with 2-bromopropionyl bromide to obtain a product represented by Formula II below:

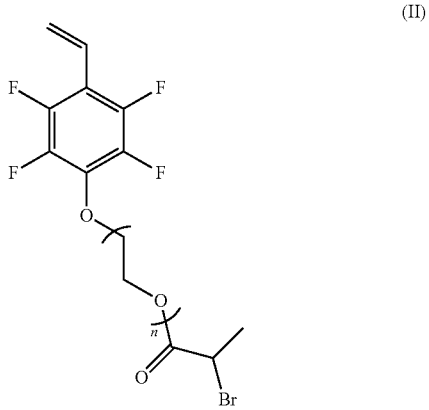

(II)

and (c) reacting the product obtained in (b) with 2,3,4,5,6-pentafluorostyrene to obtain a branched fluoropolymer represented by Formula III below:

wherein n is selected from an integer between 1 and 15 inclusive; x is selected from a number between 0.01 and 0.99, where y=(1−x); and m, q, and p are independently selected from an integer between 1 and 250 inclusive; and (d) reacting the branched fluoropolymer obtained in (c) with bisaminopropyl-polyethylene glycol having between 1 and 250 monomer units and bisaminopropyl-polydimethylsiloxane having between 1 and 250 monomer units to obtain a terpolymer of the branched fluoropolymer, polyethylene glycol and polydimethylsiloxane, wherein the weight percentage of diamino-polydimethylsiloxane is between about 0.5% and about 99% of the weight of the compound.

15. A method for preparing a compound for reducing or mitigating biofouling comprising:

(a) reacting 2,3,4,5,6-pentafluorostyrene with polyethylene glycol to obtain a product represented by Formula I below:

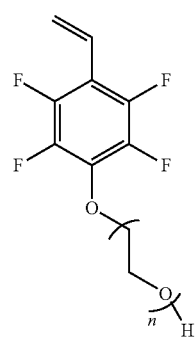

(I)

wherein n is selected from an integer between 1 and 15 inclusive;

(b) reacting the product obtained in (a) with 2-bromopropionyl bromide to obtain a product represented by Formula II below:

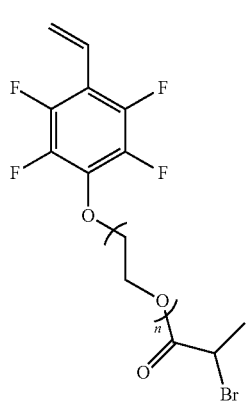

(II)

and (c) reacting the product obtained in (b) with 2,3,4,5,6-pentafluorostyrene to obtain a branched fluoropolymer represented by Formula III below:

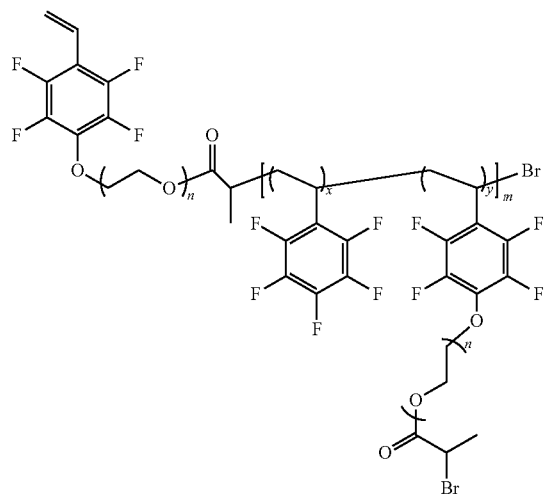

(III)

wherein n is selected from an integer between 1 and 15 inclusive; x is selected from a number between 0.01 and 0.99, where y=(1−x); and m, q, and p are independently selected from an integer between 1 and 250 inclusive; and (d) reacting the branched fluoropolymer obtained in (c) with bisaminopropyl-polyethylene glycol having between 1 and 250 monomer units and bisaminopropyl-polydimethylsiloxane having between 1 and 250 monomer units to obtain a terpolymer of the branched fluoropolymer, polyethylene glycol and polydimethylsiloxane, wherein the weight percentage of diaminopolyethylene glycol is between about 17.5% and about 30% of the weight of the compound.

16. A method for preparing a compound for reducing or mitigating biofouling comprising:

(a) reacting 2,3,4,5,6-pentafluorostyrene with polyethylene glycol to obtain a product represented by Formula I below:

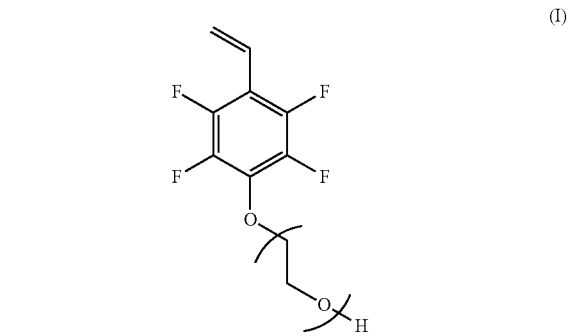

(I)

wherein n is selected from an integer between 1 and 15 inclusive;

(b) reacting the product obtained in (a) with 2-bromopropionyl bromide to obtain a product represented by Formula II below:

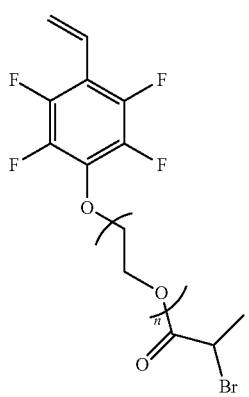

(II)

and (c) reacting the product obtained in (b) with 2,3,4,5,6-pentafluorostyrene to obtain a branched fluoropolymer represented by Formula III below:

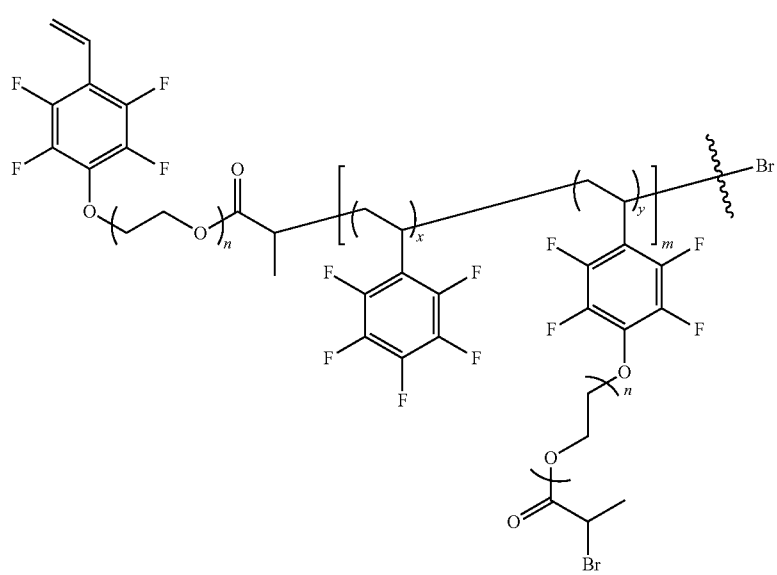

(III)

wherein n is selected from an integer between 1 and 15 inclusive; x is selected from a number between 0.01 and 0.99, where y=(1−x); and m, q, and p are independently selected from an integer between 1 and 250 inclusive; and (d) reacting the branched fluoropolymer obtained in (c) with bisaminopropyl-polyethylene glycol having between 1 and 250 monomer units and bisaminopropyl-polydimethylsiloxane having between 1 and 250 monomer units to obtain a terpolymer of the branched fluoropolymer, polyethylene glycol and polydimethylsiloxane, wherein the weight percentage of diamino-polydimethylsiloxane is between about 17.5% and about 30% of the weight of the compound.

17. A method for preparing a compound for reducing or mitigating biofouling comprising:

(a) reacting 2,3,4,5,6-pentafluorostyrene with polyethylene glycol to obtain a product represented by Formula I below:

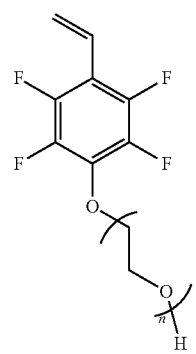

(I)

wherein n is selected from an integer between 1 and 15 inclusive;

(b) reacting the product obtained in (a) with 2-bromopropionyl bromide to obtain a product represented by Formula II below:

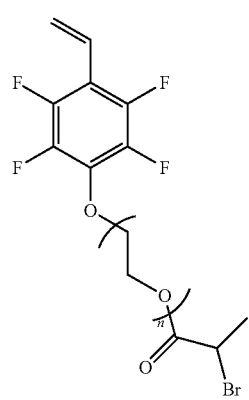

(II)

and (c) reacting the product obtained in (b) with 2,3,4,5,6-pentafluorostyrene to obtain a branched fluoropolymer represented by Formula III below:

(III)

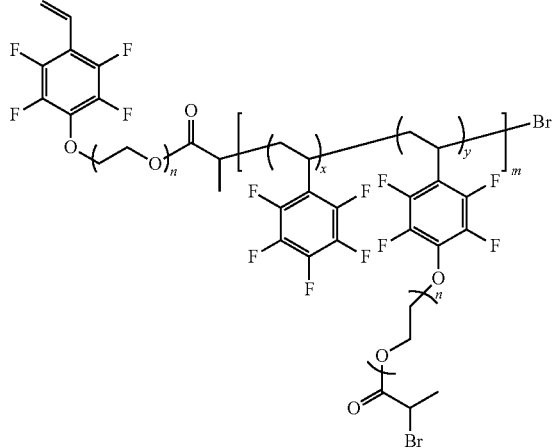

wherein n is selected from an integer between 1 and 15 inclusive; x is selected from a number between 0.01 and 0.99, where y=(1−x); and m, q, and p are independently selected from an integer between 1 and 250 inclusive; and (d) reacting the branched fluoropolymer obtained in (c) with bisaminopropyl-polyethylene glycol having between 1 and 250 monomer units and bisaminopropyl-polydimethylsiloxane having between 1 and 250 monomer units to obtain a terpolymer of the branched fluoropolymer, polyethylene glycol and polydimethylsiloxane, wherein the weight percentage of diaminopolyethylene glycol is between about 17.5% and about 30% of the weight of the compound and the weight percentage of diamino-polydimethylsiloxane is between about 17.5% and about 30% of the weight of the compound.

18. The composition of claim 1, further comprising one or more of an adhesion agent, a dispersant, a solvent, and a stabilizer.

19. The composition of claim 2, wherein the compound comprises a heterogeneous distribution of chemical domains.

20. The composition of claim 19, wherein the compound comprises a heterogeneous distribution of hydrophobic and hydrophilic domains.

21. The composition of claim 2, wherein the compound exhibits topographical heterogeneity at the microscale and at the nanoscale.

22. The composition of claim 2, wherein the compound comprises a raised region, a lattice region, and a deeper interstitial region.

23. The composition of claim 22, wherein
the raised region is characterized by a high modulus, a low deformation, a low surface energy, and low dissipation;
the lattice region is characterized by a moderate modulus, a moderate deformation, a low surface energy, and a moderate dissipation; and
the deeper interstitial region is characterized by a low modulus, a high deformation, a high surface energy, and a high dissipation.

24. The composition of claim 2, further comprising one or more of an adhesion agent, a dispersant, a solvent, and a stabilizer.

25. The composition of claim 3, wherein the compound comprises a heterogeneous distribution of chemical domains.

26. The composition of claim 25, wherein the compound comprises a heterogeneous distribution of hydrophobic and hydrophilic domains.

27. The composition of claim 3, wherein the compound exhibits topographical heterogeneity at the microscale and at the nanoscale.

28. The c composition of claim 3, wherein the compound comprises a raised region, a lattice region, and a deeper interstitial region.

29. The composition of claim 28, wherein
the raised region is characterized by a high modulus, a low deformation, a low surface energy, and low dissipation;
the lattice region is characterized by a moderate modulus, a moderate deformation, a low surface energy, and a moderate dissipation; and
the deeper interstitial region is characterized by a low modulus, a high deformation, a high surface energy, and a high dissipation.

30. The composition of claim 3, further comprising one or more of an adhesion agent, a dispersant, a solvent, and a stabilizer.

31. The composition of claim 4, wherein the compound comprises a heterogeneous distribution of chemical domains.

32. The composition of claim 29, wherein the compound comprises a heterogeneous distribution of hydrophobic and hydrophilic domains.

33. The composition of claim 4, wherein the compound exhibits topographical heterogeneity at the microscale and at the nanoscale.

34. The composition of claim 4, wherein the compound comprises a raised region, a lattice region, and a deeper interstitial region.

35. The composition of claim 34, wherein
the raised region is characterized by a high modulus, a low deformation, a low surface energy, and low dissipation;
the lattice region is characterized by a moderate modulus, a moderate deformation, a low surface energy, and a moderate dissipation; and
the deeper interstitial region is characterized by a low modulus, a high deformation, a high surface energy, and a high dissipation.

36. The composition of claim 4, further comprising one or more of an adhesion agent, a dispersant, a solvent, and a stabilizer.

37. The composition of claim 5, wherein the compound comprises a heterogeneous distribution of chemical domains.

38. The composition of claim 37, wherein the compound comprises a heterogeneous distribution of hydrophobic and hydrophilic domains.

39. The composition of claim 5, wherein the compound exhibits topographical heterogeneity at the microscale and at the nanoscale.

40. The composition of claim 5, wherein the compound comprises a raised region, a lattice region, and a deeper interstitial region.

41. The composition of claim 40, wherein
the raised region is characterized by a high modulus, a low deformation, a low surface energy, and low dissipation;
the lattice region is characterized by a moderate modulus, a moderate deformation, a low surface energy, and a moderate dissipation; and the deeper interstitial region is characterized by a low modulus, a high deformation, a high surface energy, and a high dissipation.

42. The method of claim 14, wherein the terpolymer of the branched fluoropolymer, polyethylene glycol and polydimethylsiloxane obtained is represented by the compound of Formula A below

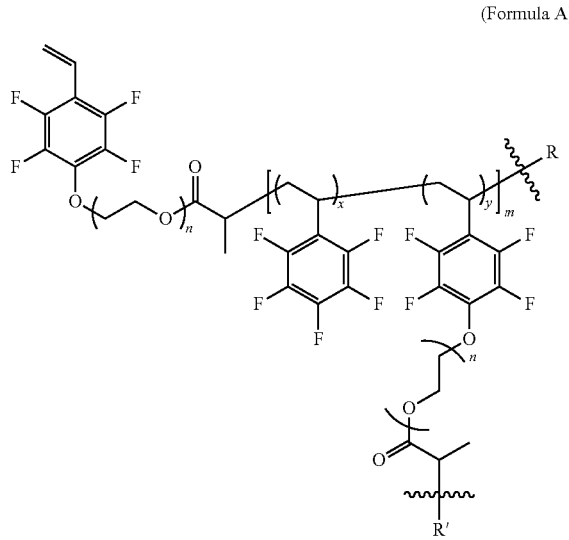

(Formula A)

wherein R is selected from the group consisting of

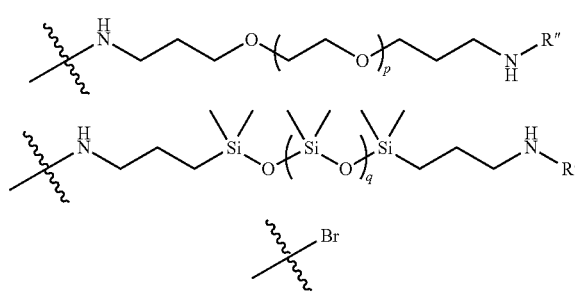

and R' is selected from the group consisting of

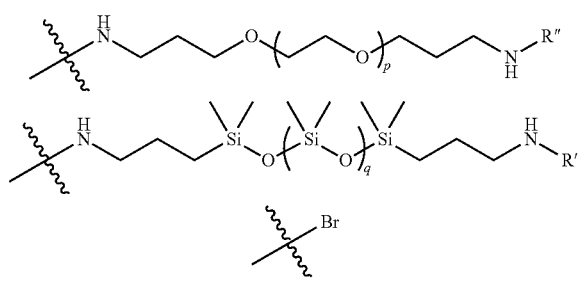

wherein R" is another domain of Formula A or Hydrogen.

43. The method of claim 14, wherein the terpolymer of the branched fluoropolymer, polyethylene glycol and polydimethylsiloxane is represented by Compound Q.

44. The method of claim 15, wherein the terpolymer of the branched fluoropolymer, polyethylene glycol and polydimethylsiloxane obtained is represented by the compound of Formula A below

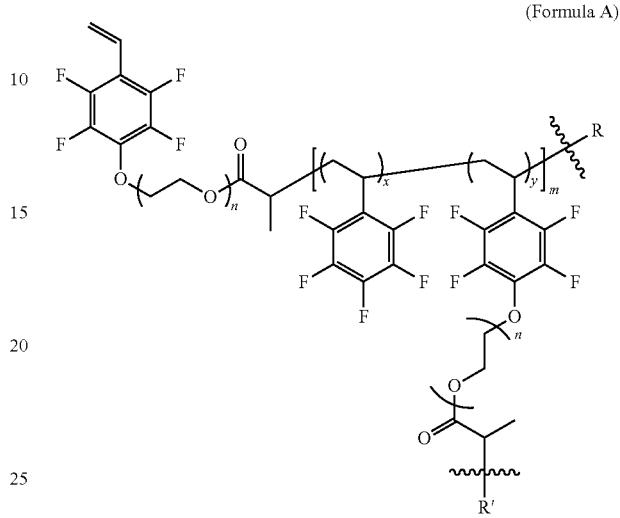

(Formula A)

wherein R is selected from the group consisting of

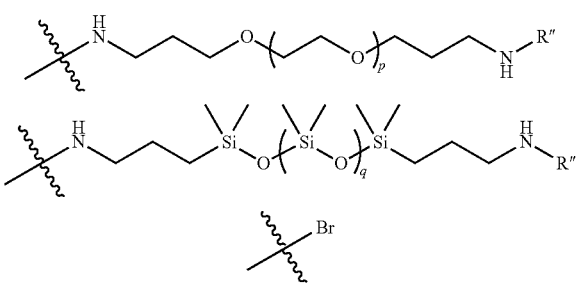

and R' is selected from the group consisting of

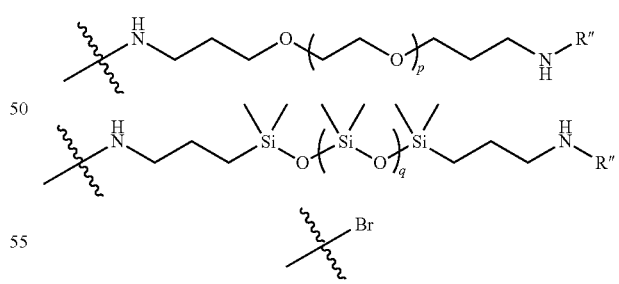

wherein R" is another domain of Formula A or Hydrogen.

45. The method of claim 15, wherein the terpolymer of the branched fluoropolymer, polyethylene glycol and polydimethylsiloxane is represented by compound Q.

46. The method of claim 16, wherein the terpolymer of the branched fluoropolymer, polyethylene glycol and polydimethylsiloxane obtained is represented by the compound of Formula A below (Formula A)

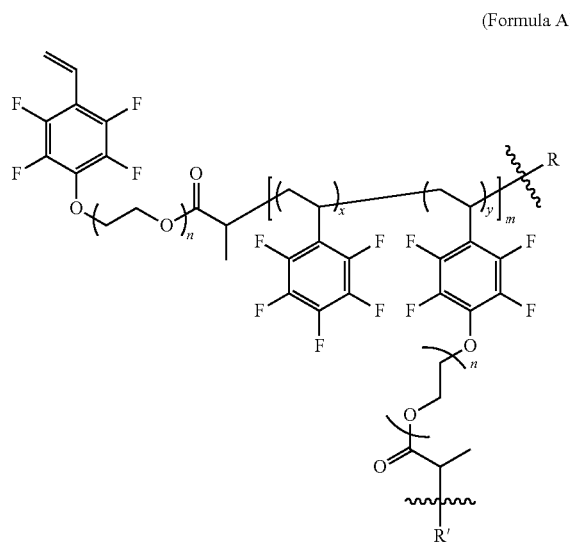

wherein R is selected from the group consisting of

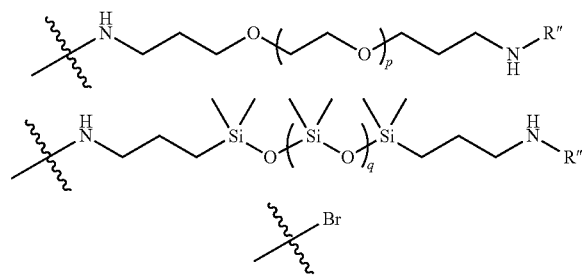

and R' is selected from the group consisting of

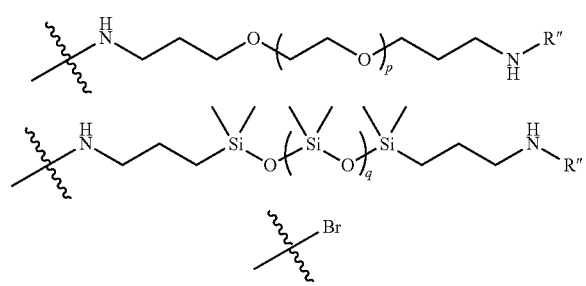

wherein R" is another domain of Formula A or Hydrogen.

47. The method of claim 16, wherein the terpolymer of the branched fluoropolymer, polyethylene glycol and polydimethylsiloxane is represented by Compound Q.

48. The method of claim 17, wherein the terpolymer of the branched fluoropolymer, polyethylene glycol and polydimethylsiloxane obtained is represented by the compound of Formula A below (Formula A)

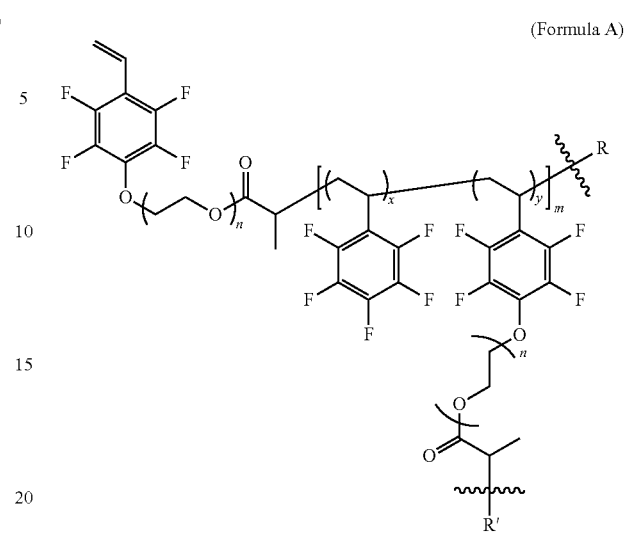

wherein R is selected from the group consisting of

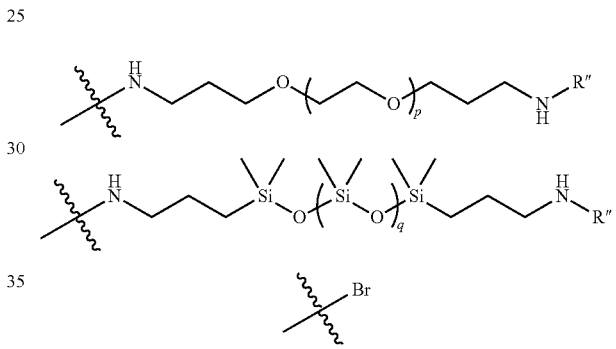

and R' is selected from the group consisting of

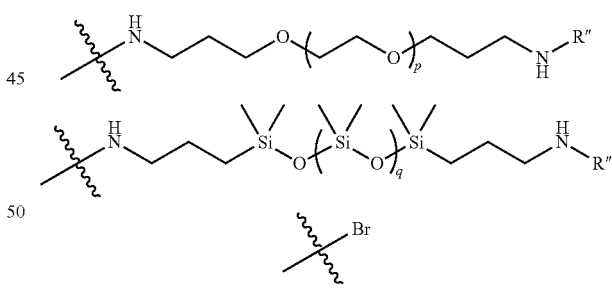

wherein R" is another domain of Formula A or Hydrogen.

49. The method of claim 17, wherein the terpolymer of the branched fluoropolymer, polyethylene glycol and polydimethylsiloxane is represented by Compound Q.

* * * * *